United States Patent [19]
Ohira et al.

[11] Patent Number: 6,084,081
[45] Date of Patent: Jul. 4, 2000

[54] LEWIS X DERIVATIVES

[75] Inventors: Yutaka Ohira; Takao Iida, both of Tsukuba, Japan

[73] Assignee: Daikin Industries, Ltd., Osaka, Japan

[21] Appl. No.: 09/254,670

[22] PCT Filed: Sep. 12, 1997

[86] PCT No.: PCT/JP97/03247

§ 371 Date: May 6, 1999

§ 102(e) Date: May 6, 1999

[87] PCT Pub. No.: WO98/11118

PCT Pub. Date: Mar. 19, 1998

[30] Foreign Application Priority Data

Sep. 13, 1996 [JP] Japan .................................. 8-242972

[51] Int. Cl.[7] .................... C07H 15/00; C07H 17/00
[52] U.S. Cl. .................... 536/17.6; 536/17.1; 536/17.2; 536/17.4; 536/17.5; 536/18.7; 536/54
[58] Field of Search ................... 536/17.2, 17.4, 536/17.5, 17.6, 17.1, 18.7, 54

[56] References Cited

FOREIGN PATENT DOCUMENTS

| 616692 | 1/1997 | Japan . |
|---|---|---|
| 9323031 | 11/1993 | WIPO . |

OTHER PUBLICATIONS

A. Hasegawa et al., Synthesis of sialyl Lewis X ganglioside and analogs. Methods Enzymol., vol. 242 (1994 p. 158–173.

Y. Wada et al., Studies on selectin blockers. 2. Novel selectin blocker as potential therapeutics for inflammatory disorders. J. Med. Chem., vol. 39 (1996. May) p. 2055–2059.

H. Ohmoto et al., Studies on selectin blocker. 1. Structure--activity relationships of sialyl Lewis X analogs. J. Med. Chem., vol. 39 (1996. Mar.) p. 1339–1343.

A. Hasegawa et al., Synthetic studies on sialoglycoconjugates 70: Synthesis of Sialyl and sulfo Lewis X analogs containing a ceramide or 2-(tetradecyl) hexadecyl residue. J. Carbohydr. Chem. vol. 14, No. 3 (1995) p. 353–368.

*Primary Examiner*—Elli Peselev
*Attorney, Agent, or Firm*—Baker Botts L.L.P.

[57] ABSTRACT

A novel fluorine-containing Lewis X derivative represented by the following formula (I):

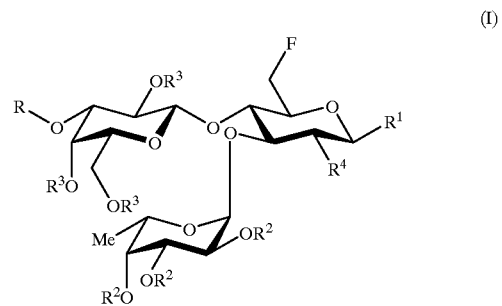

wherein R represents hydrogen, a hydroxyl-protective group, $-PO(OH)_2$, $-SO_3H$ or sialylate;

$R^1$ represents hydrogen, hydroxyl, aliphatic acyloxy, aromatic acyloxy, lower alkylthio, optionally substituted phenylthio, lower alkoxy, branched long chain alkoxy, optionally substituted phenylmethoxy or sphingosinyl, $R^{10}$ represents hydrogen or $-O-C-(=NH)CCl_3$; provided that when $R^{10}$ is $-O-C-(=NH)CCl_3$, $R^9$ is hydrogen;

$R^2$ and $R^3$ are the same or different and independently represent hydrogen, aliphatic acyl, aromatic acyl or optionally substituted phenylmethyl; and $R^4$ represents hydroxyl, aliphatic acyloxy, aromatic acyloxy, aliphatic acylamino or aromatic acylamino.

8 Claims, 1 Drawing Sheet

LEWIS X DERIVATIVES

FIELD OF THE INVENTION

The present invention relates to a Lewis X derivative in which hydroxyl at 6-position of N-acetylglucosamine is substituted with fluorine, and to a synthetic intermediate thereof. This derivative and synthetic intermediate are useful, for example, as a sugar chain-related physiologically active substance and an intermediate for synthesis thereof.

In this specification, Ac denotes acetyl, Me denotes methyl, Bz denotes benzoyl and Bn denotes benzyl.

BACKGROUND ART

Sialyl Lewis X sugar chain, which is an oligosaccharide containing fucose, has recently attracted attention as a molecule involved in homing phenomena in which upon inflammation, leukocytes interact with vascular endothelial cells and bleed out of the blood vessel.

Some of the homing phenomena start with interaction of the sialyl Lewis X oligosaccharide with a lectin-like cell adhesion molecule called selectin. Therefore, if the sialyl Lewis X oligosaccharide can be used as a selectin binding inhibitor, it is expected to suppress acute inflammations depending on neutrophils (one of leucocytes) and on selectin. In fact, a group of the University of Michigan demonstrated that administration of sialyl Lewis X sugar chain (3) ameliorates acute pulmonary inflammation that has been experimentally induced in rats using a cobra venom factor [M. S. Mulligan et al., Nature 364, 149 (1993)].

Later, as a result of synthesis of various sialyl Lewis X derivatives and study about their structure-activity relationship, it became clear that the following portions are important as counter ligands: (i) carboxylic acid of sialic acid, (ii) the residue of fucose and (iii) hydroxyl groups at 4- and 6-positions of galactose. Also concerning inhibitory activity against one of the selectins called P-selectin, recent work has revealed that a sugar chain (4) deoxidized at 1-position of the reducing terminal is about 20 times as potent in inhibitory activity as the above sugar chain (3). Furthermore, a potent selectin blocker "GSC-150" (5) has been developed by synthesis of a Lewis X derivative by substituting sialic acid of a sialyl Lewis X with an acidic functional group (e.g., sulfonic acid, phosphoric acid, carboxylic acid, etc.) and subsequent study of its selectin-adhesion inhibitory activity. A branched long chain alkyl exists at a reducing terminal of this compound, and this portion is thought to play a key role in expression of the inhibitory activity [H. Kondo et al., Journal of Medicinal Chemistry 39, 1339 (1996); H. Kondo et al., Journal of Medicinal Chemistry 39, 2055 (1996); A. Hasegawa et al., Journal of Carbohydrate Chemistry 14, 353 (1995).

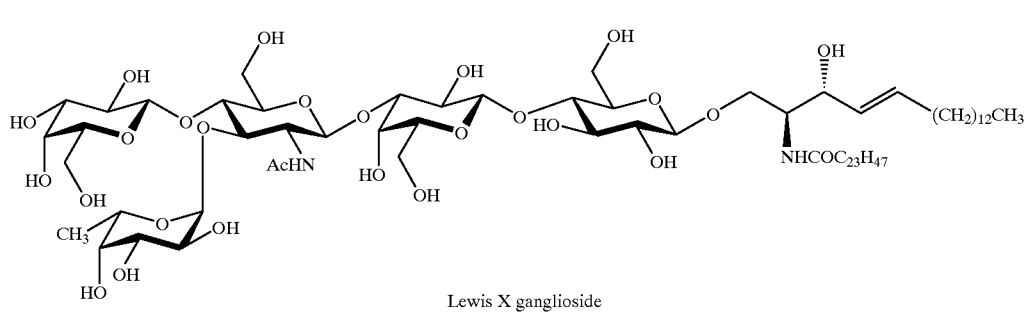

Lewis X ganglioside (1)

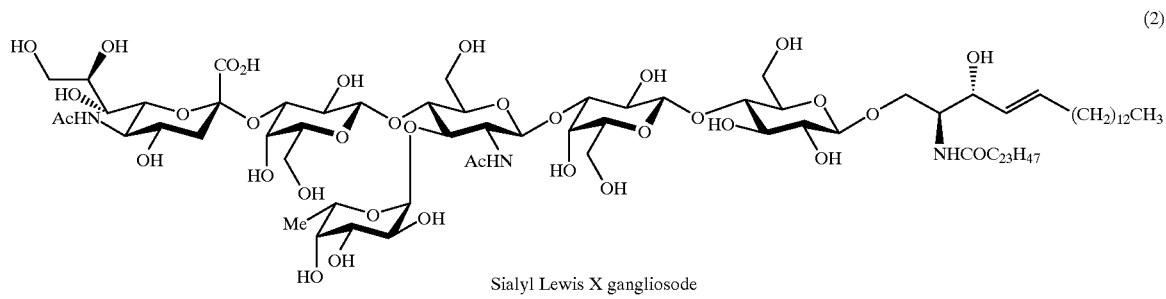

Sialyl Lewis X gangliosode (2)

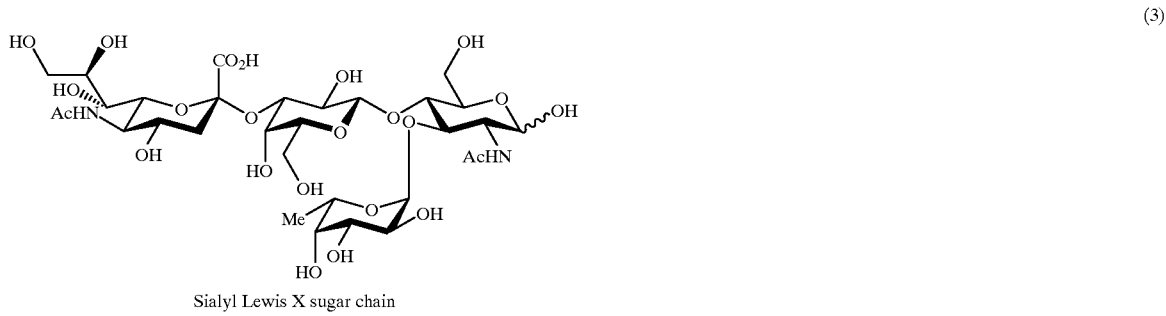

Sialyl Lewis X sugar chain (3)

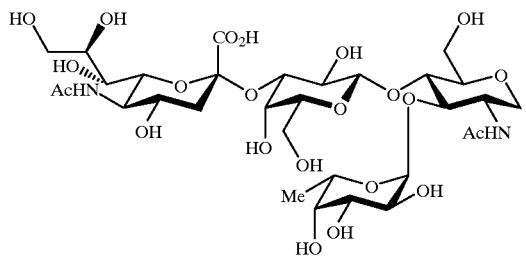

1-Deoxy sialyl Lewis X sugar chain (4)

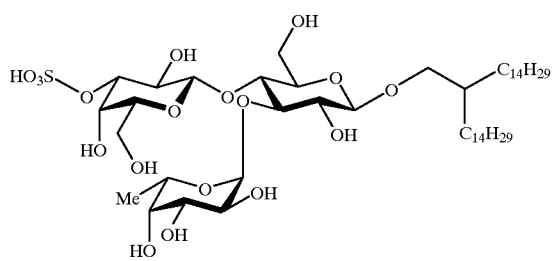

GSC-150

(5)

As seen from the above, Lewis X derivatives are known as ligand portions of E-, P- or L-selectin having action as a cell adhesion molecule, and are important compounds having a function as a recognition element of cells specifically expressing these selectins. It is meaningful to synthesize sialyl Lewis X derivatives modified with fluorine in an organic chemical manner and to provide them in practical amounts.

As such a compound, the present inventors conceived a Lewis X derivative having fluorine in place of hydroxyl at 6-position of N-acetylglucosamine. However, there was no known method for position-selective fluorination to synthesize a Lewis X sugar chain in which hydroxyl at 6-position of N-acetylglucosamine is fluorinated.

An object of the present invention is to provide a new fluorine-containing Lewis X derivative and a synthetic intermediate thereof.

The fluorine-containing Lewis X derivative and the synthetic intermediate according to the invention are useful as a 6-fluorine derivative and an intermediate for synthesis of its analogues, the 6-fluorine derivative possessing improved metabolic stability as compared with conventional selectin blockers such as 1-deoxy sialyl Lewis X (4) and GSC-150 (5).

The fluorine-containing Lewis X derivative of the invention has selectin inhibitory activity because it contains (i) carboxylic acid of sialic acid, (ii) the residue of fucose and (iii) hydroxyl groups at 4- and 6-positions of galactose, which are necessary portions for activities of sialyl Lewis X derivatives. Moreover, because of fluorination of 6-position of N-acetylglucosamine, the position being prone to be modified metabolically, the derivative of the invention has the advantage of exhibiting improved metabolic stability in vivo as a physiologically active substance.

DISCLOSURE OF THE INVENTION

Figure 1:
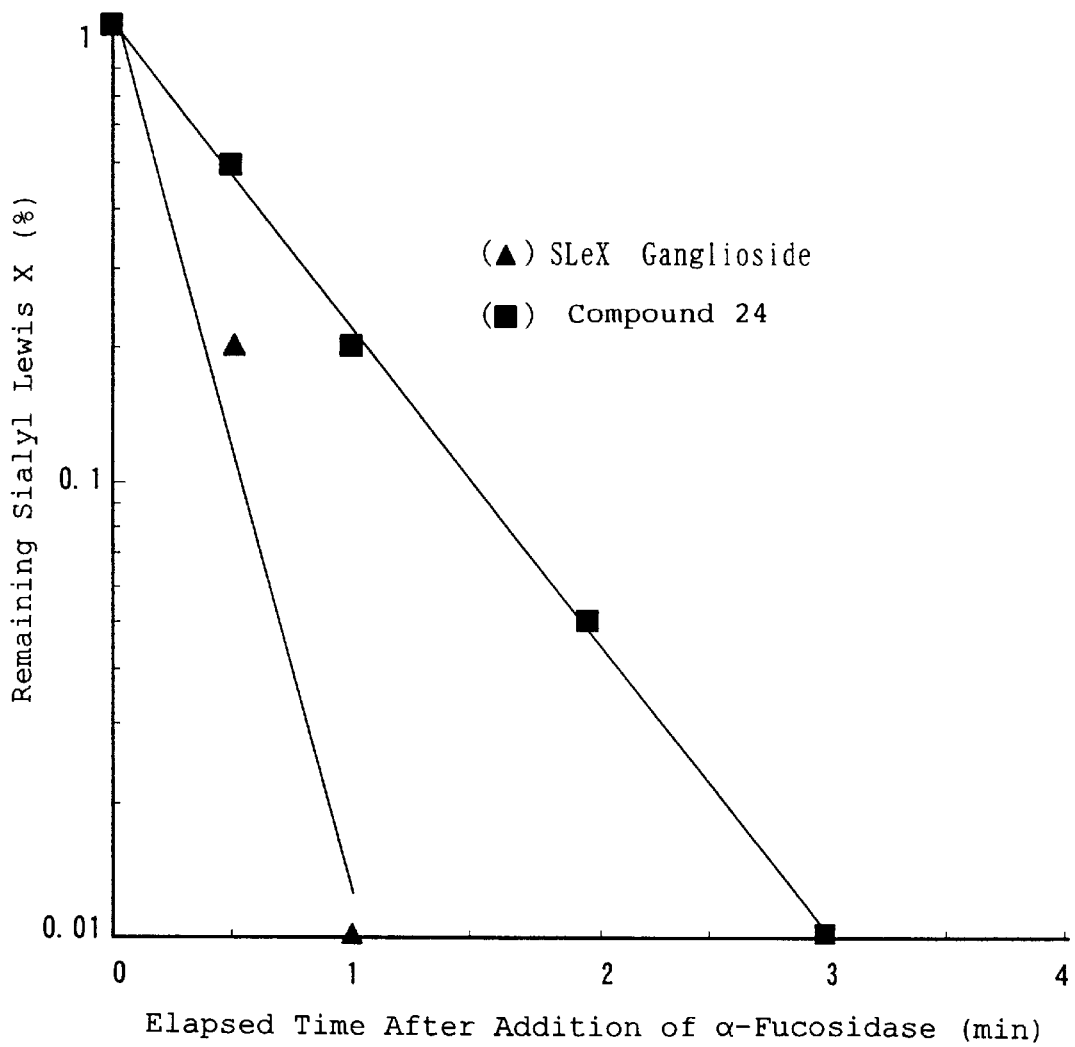
FIG. 1 shows the results of decomposition of compound 24 of the invention (■) and a natural sialyl Lewis X Ganglioside (SLeX Ganglioside; ▲) by α-fucosidase.

The present inventor carried out research to synthesize a Lewis X analogue in which hydroxyl at 6-position of N-acetylglucosamine is chemically modified with fluorine, and finally succeeded in its synthesis and completed the present invention.

Thus the present invention provides a compound represented by the following formula (I):

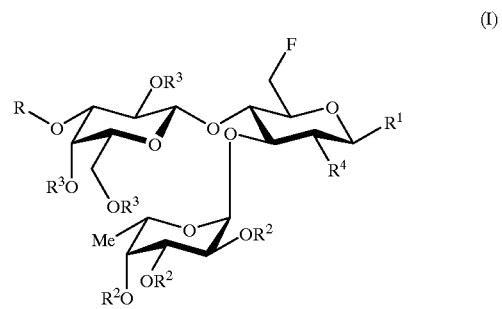

(I)

wherein R represents hydrogen, a hydroxyl-protective group, $-PO(OH)_2$, $-SO_3H$ or sialylate represented by formula (III)

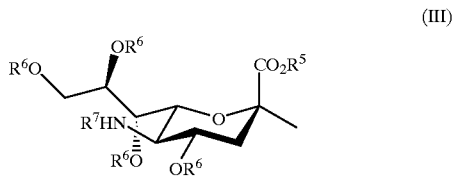

(III)

wherein $R^5$ represents hydrogen, lower alkyl, sodium, potassium or quaternary ammonium, $R^6$ represents hydrogen, aliphatic acyl or aromatic acyl and $R^7$ represents aliphatic acyl.

$R^1$ represents hydrogen, hydroxyl, aliphatic acyloxy, aromatic acyloxy, lower alkylthio, optionally substituted phenylthio, lower alkoxy, branched long chain alkoxy, optionally substituted phenylmethoxy or formula (IV)

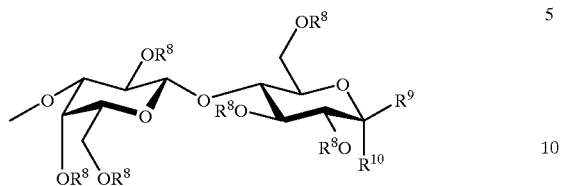
(IV)

wherein $R^8$ represents hydrogen, aliphatic acyl, aromatic acyl or optionally substituted phenylmethyl, $R^9$ represents hydrogen, hydroxyl, trialkylsilylethoxy or sphingosinyl represented by formula (V)

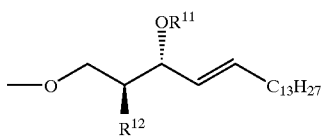
(V)

wherein $R^{11}$ represents hydrogen or benzoyl, $R^{12}$ represents azide, amine or —NHCOR$^{13}$ and $R^{13}$ represents $C_{15\text{-}25}$ aliphatic alkyl, and
$R^{10}$ represents hydrogen or —O—C(=NH)CCl$_3$, provided that when $R^{10}$ is —O—C(=NH)CCl$_3$, $R^9$ is hydrogen.

$R^2$ and $R^3$ may be the same or different and independently represent hydrogen, aliphatic acyl, aromatic acyl or optionally substituted phenylmethyl.

$R^4$ represents hydroxyl, aliphatic acyloxy, aromatic acyloxy, aliphatic acylamino or aromatic acylamino.

The present invention further provides an intermediate for synthesis of a sialyl Lewis X derivative or a Lewis X derivative, which is represented by the following formula (II):

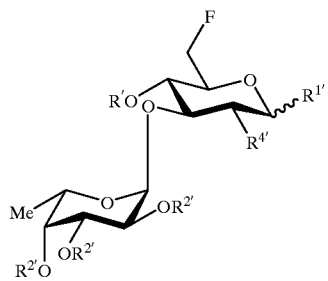
(II)

wherein R' represents hydrogen, aliphatic acyl or aromatic acyl; $R^{1'}$ represents hydrogen, hydroxyl, optionally substituted phenylmethoxy, aliphatic acyloxy, aromatic acyloxy, lower alkylthio, optionally substituted phenylthio, lower alkoxy or branched long chain alkoxy; $R^{2'}$ represents hydrogen, optionally substituted phenylmethyl, aliphatic acyl or aromatic acyl; and $R^{4'}$ represents hydroxyl, optionally substituted phthalimide, aliphatic acyloxy, aromatic acyloxy, aliphatic acylamino or aromatic acylamino.

Preferably, the present invention provides the following sialyl Lewis X derivatives, Lewis X derivatives and α-fucosyl-(1→3)-glucosamine derivatives:

sialyl Lewis X derivatives of the following formulae (VI), (VII), (VIII) and (IX):

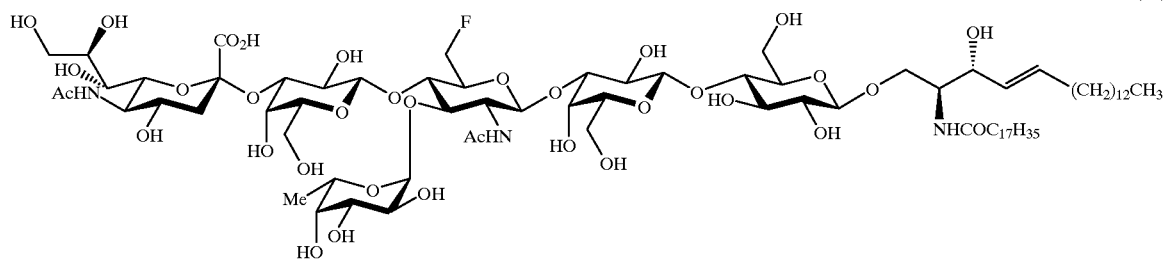
(VI)

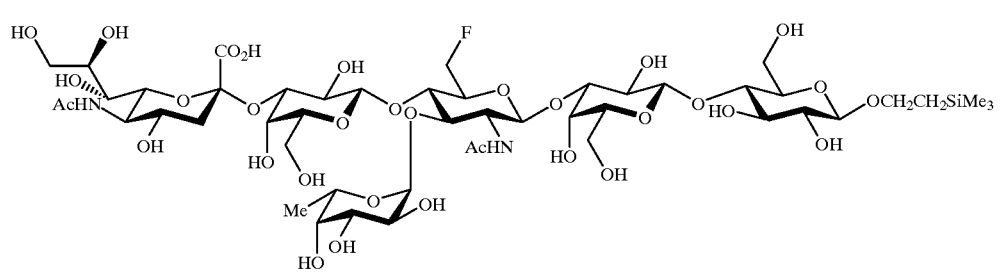
(VII)

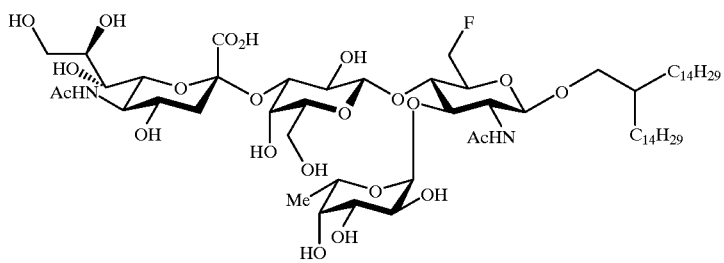
(VIII)
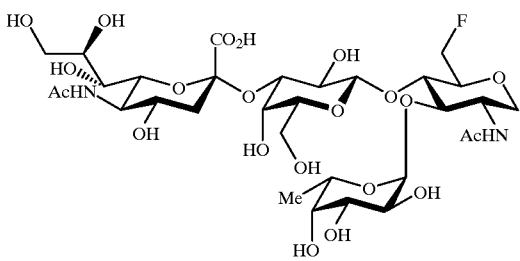
(IX)
Lewis X derivatives of the following formula (X):
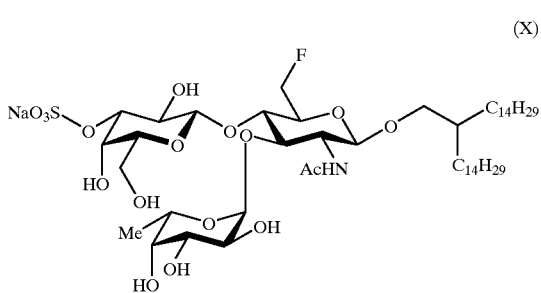
(X)
α-fucosyl-(1→3)-glucosamine derivatives of the following formulae (XI), (XII), (XIII), (XIV) and (XVI)
(XI)
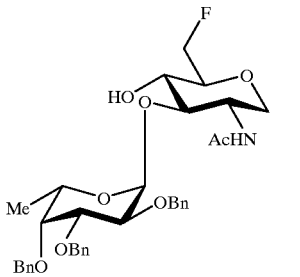
-continued
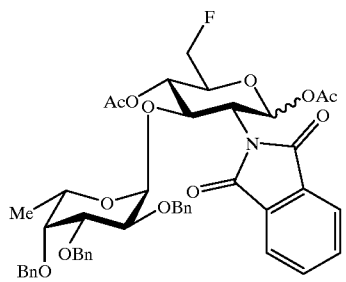
(XII)
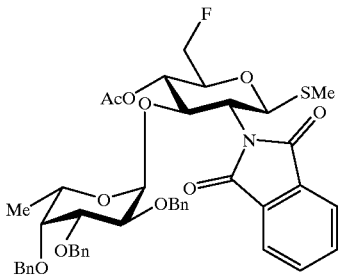
(XIII)
(XIV)

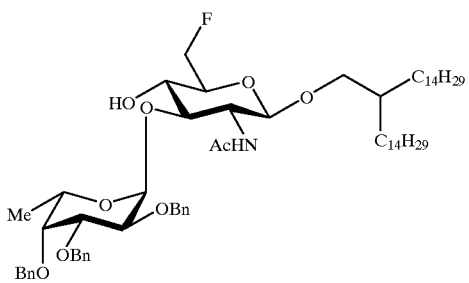

(XVI)

Since the derivative of formula (XI) has different protective groups at 1-, 2- and 4-positions of glucosamine, selective deprotection can be achieved. Thus it is possible to selectively introduce any compound such as monosaccharide, oligosaccharide, carboxylic acid, sulfonic acid or phosphoric acid to 1-, 2- or 4-position. The derivative of formula (XI) is useful as an intermediate for chemical synthesis of fluorinated Lewis X sugar chain. These compounds have not been described in any literature.

In the compound of formula (I), R represents hydrogen, a hydroxyl-protective group, —PO(OH)$_2$, —SO$_3$H, or a compound of formula (III), of which hydrogen or a compound of formula (III) (wherein R$^5$ is methyl or hydrogen, R$^6$ is acetyl or hydrogen and R$^7$ is acetyl) is preferred.

Examples of hydroxyl-protective groups are acetyl, propionyl, butyryl, benzyl, benzoyl, t-butyldimethylsilyl, t-butyldiphenylsilyl, trimethylsilylethyl, tetrahydropyranyl and the like.

R$^1$ represents hydrogen, hydroxyl, aliphatic acyloxy, aromatic acyloxy, lower alkylthio, optionally substituted phenylthio, lower alkoxy, branched long chain alkoxy, optionally substituted phenylmethoxy or a compound of formula (IV), of which hydrogen, hydroxyl and a compound of formula (IV) are preferred.

Examples of aliphatic acyloxy groups represented by R$^1$, R$^4$, R$^{1'}$ and R$^{4'}$ are C$_{2-5}$ acyloxy groups, for example, acetyloxy, propionyloxy, butyryloxy, isobutyryloxy, valeryloxy, isovaleryloxy, pivaloyloxy and the like.

Examples of aromatic acyloxy groups represented by R$^1$, R$^4$, R$^{1'}$ and R$^{4'}$ are benzoyloxy, p-methoxybenzoyloxy, naphthoyloxy, toluoyloxy and the like.

Examples of lower alkylthio groups represented by R$^1$ and R$^{1'}$ are straight or branched C$_{1-9}$ alkylthio groups, for example, methylthio, ethylthio, n-propylthio, isopropylthio, n-butylthio, isobutylthio, sec-butylthio, tert-butylthio, n-octylthio and the like.

Examples of lower alkoxy groups represented by R$^1$ and R$^{1'}$ are straight or branched C$_{1-9}$ alkoxy groups, for example, methoxy, ethoxy, n-propoxy, isopropoxy, n-butoxy, isobutoxy, sec-butoxy, tert-butoxy, n-hexyloxy, n-octyoxy, n-nonyloxy and the like.

Examples of branched long chain alkoxyl groups represented by R$^1$ and R$^{1'}$ are alkoxyl groups represented by the formula —OCH$_2$CH(C$_n$H$_{2n+1}$)$_2$ (wherein n is an integer of 9 to 20), for example, C$_{20-42}$ branched long chain alkoxy groups such as —OCH$_2$CH(C$_{14}$H$_{29}$)$_2$.

Examples of optionally substituted phenylmethoxy groups represented by R$^1$, R$^8$ and R$^{1'}$ are phenylmethoxy groups which may have 1–2 substituents selected from the group consisting of C$_{1-4}$ alkyl, C$_{1-4}$ alkoxy, halogen and nitro, for example, phenylmethoxy, p-methylphenylmethoxy, p-nitrophenylmethoxy, p-methoxyphenylmethoxy, p-chlorophenylmethoxy, 3,4-dimethoxyphenylmethoxy, p-cyanophenylmethoxy and the like.

R$^2$ and R$^3$ may be the same or different and independently represent hydrogen, aliphatic acyl, aromatic acyl or optionally substituted phenylmethyl, of which hydrogen is preferred.

Examples of aliphatic acylic groups represented by R$^2$, R$^3$, R$^6$, R$^7$, R$^8$ and R' are C$_{2-5}$ aliphatic acylic groups, for example, acetyl, propionyl, butyryl, isobutyryl, valeryl, isovaleryl, pivaloyl and the like.

Examples of aromatic acylic groups represented by R$^2$, R$^3$, R$^6$, R$^8$ and R' are aromatic acylic groups which may have 1 or 2 substitutents selected from the group consisting of C$_{1-4}$ alkyl, C$_{1-4}$ alkoxy, halogen and nitro, for example, benzoyl, p-methoxybenzoyl, naphthoyl, toluoyl, p-nitrobenzoyl, 3,4-dimethoxybenzoyl and the like.

R$^4$ represents hydroxyl, aliphatic acyloxy, aromatic acyloxy, aliphatic acylamino or aromatic acylamino, of which acetylamino is preferred.

Examples of aliphatic acylamino groups represented by R$^4$ and R$^{4'}$ are C$_{2-5}$ aliphatic acylamino groups, for example, acetylamino, propionylamino, butyrylamino, isobutyrylamino, valerylamino, isovalerylamino, pivaloylamino and the like.

Examples of aromatic acylamino groups represented by R$^4$ and R$^{4'}$ are aromatic acylamino groups which may have 1 or 2 substituents selected from the group consisting of C$_{1-4}$ alkyl, C$_{1-4}$ alkoxy and halogen, for example, benzoylamino, p-methoxybenzoylamino, naphthoylamino, toluoylamino, p-chlorobenzoylamino and the like.

In the compound of formula (III), R$^5$ represents hydrogen, lower alkyl, sodium, potassium or a quaternary ammonium group (e.g., tetramethylammonium, tetraethylammonium), of which hydrogen is preferred.

Examples of lower alkyl groups represented by R$^5$ are straight or branched C$_{1-8}$ alkyl groups, for example, methyl, ethyl, n-propyl, isopropyl, n-butyl, isobutyl, sec-butyl, tert-butyl, n-octyl and the like.

In the compound of formula (IV), R$^8$ represents hydrogen, aliphatic acyl, aromatic acyl or optionally substituted phenylmethoxy, of which hydrogen is preferred. R$^9$ represents hydrogen, hydroxyl, trialkylsilylethoxy, or a compound of formula (V), of which a compound of formula (V) is preferred.

Examples of trialkylsilylethoxy groups represented by R$^9$ are trimethylsilylethoxy, triethylsilylethoxy, tripropylsilylethoxy and the like.

In the compound of formula (V), R$^{11}$ represents hydrogen or benzoyl, of which hydrogen is preferred. R$^{12}$ represents azide, amine or sphingosinyl represented by —NHCOR$^{13}$, of which sphingosinyl represented by —NHCOR$^{13}$ is preferred. R$^{10}$ represents hydrogen or —O—C(=NH)CCl$_3$, of which hydrogen is preferred.

Examples of $C_{15-25}$ aliphatic alkyl groups represented by $R^{13}$ are straight or branched $C_{15-25}$ aliphatic alkyl groups, for example, pentadecyl, heptadecyl, nonadecyl, eicosyl, tricosyl and the like.

In the compound of formula (II), R' represents hydrogen, aliphatic acyl or aromatic acyl, of which hydrogen is preferred. $R^{1'}$ represents hydrogen, hydroxyl, optionally substituted phenylmethoxy, aliphatic acyloxy, aromatic acyloxy, lower alkylthio, optionally substituted phenylthio, lower alkoxy or branched long chain alkoxy, of which hydrogen or a branched long chain alkoxy group is preferred. $R^{2'}$ represents hydrogen, optionally substituted phenylmethyl, aliphatic acyl or aromatic acyl, of which hydrogen is preferred. $R^{4'}$ represents hydroxyl, optionally substituted phthalimide, aliphatic acyloxy, aromatic acyloxy, aliphatic acylamino or aromatic acylamino, of which optionally substituted phthalimide is preferred.

Examples of phthalimide groups represented by $R^{4'}$ are phthalimide, 3,6-dichlorophthalimide, 3,4,5,6-tetrachlorophthalimide and the like.

The fluorinated Lewis X derivative of the invention contains galactose, fucose and glucosamine lactose portions as essential components, as shown in formulae (I), (VI)–(X).

Of the Lewis X derivatives, the present inventors first synthesized a fluorine-containing fucosylglucosamine p-methoxybenzyl compound (XI) and prepared therefrom a new compound of the following formula (XIII), which was then reacted with a known compound of the following formula (XVII) to produce a compound (XV), to which sialyl galactose was further introduced to give a sialyl Lewis X sugar chain (XVIII).

Subsequently a ceramide portion was introduced to give the first desired compound (VI).

First, a fluorine-containing α-fucosyl-(1→3)-glucosamine derivative of formula (II) is synthesized according to the reaction steps shown below in Reaction Scheme 1. When $R^4$ is phthalimide, for example, methyl 2-deoxy-2-phthalimide-1-thio-3,4,6-triacetyl-β-D-glucopyranose as a starting material is reacted with p-methoxybenzyl alcohol in the presence of a condensation promotor such as N-iodosuccinimide-scandium trifluoromethanesulfonate. The resulting p-methoxybenzylglycoside is deacetlylated, benzylidenated and α-fucosylated, followed by elimination of benzylidene. The resulting compound is fluorinated with a fluorinating agent (diethylaminosulfurtrifluoride) to give a compound wherein only 6-postion is fluorinated (corresponding to formula (XI) of the invention). Here, alternatively, $R^4$ may be 3,4,5,6-tetrachlorophthalimide, 4,5-dichlorophthalimide or the like.

Reaction Scheme 1

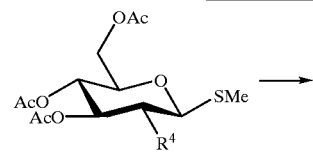

(XVII)

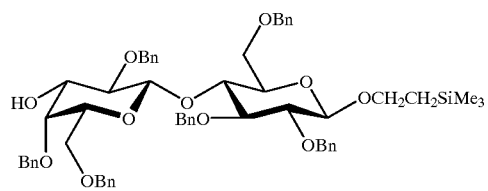

(XV)

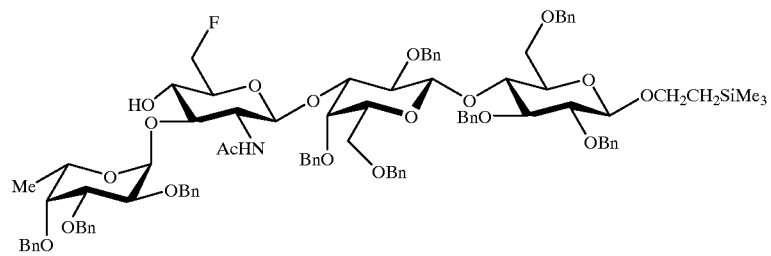

(XVIII)

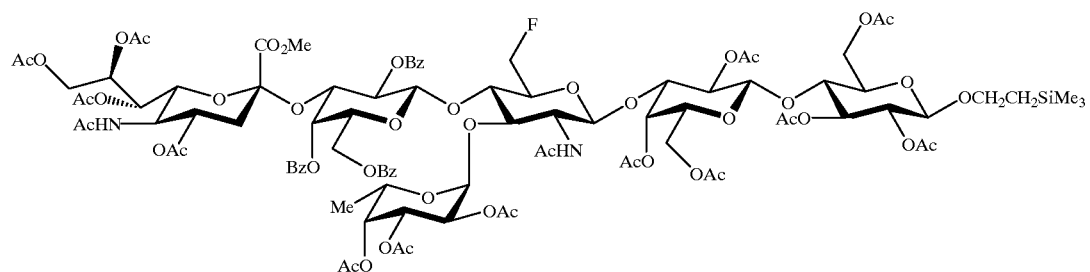

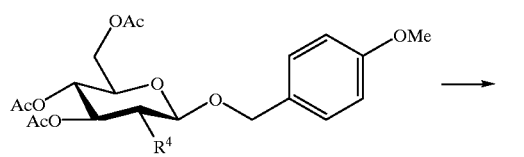

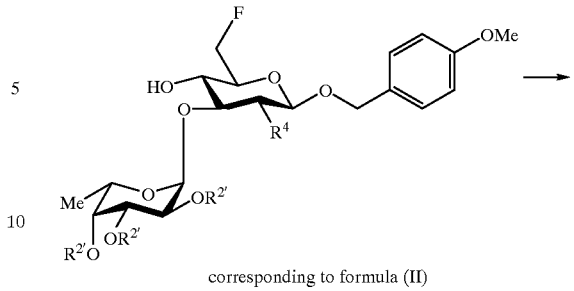

corresponding to formula (II)

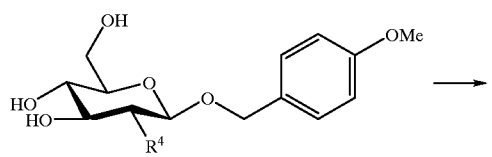

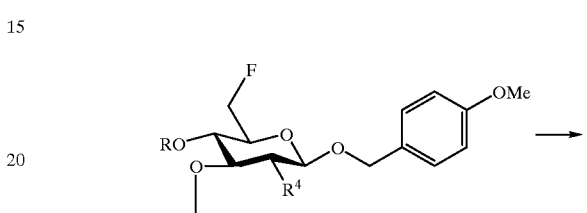

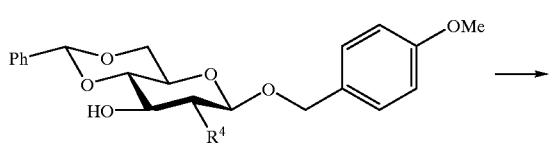

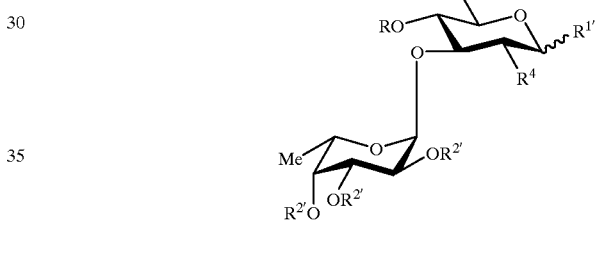

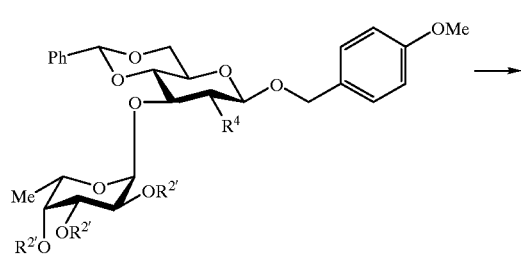

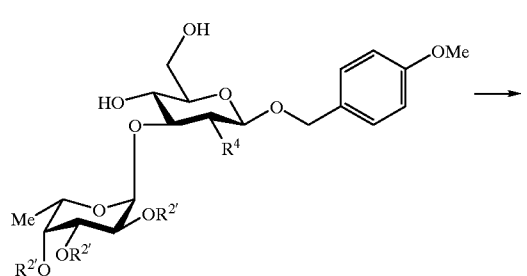

More specifically, fluorine-containing α-fucosyl-(1→3)-glucosamine derivatives (compounds (7), (8) and (9)) are synthesized according to the reaction steps shown below in Reaction Scheme 2. A commercially available methyl 2-deoxy-2-phthalimide-1-thio-3,4,6-triacetyl-β-D-glucopyranose as a starting material is treated with p-methoxybenzyl alcohol using N-iodosuccinimide-scandium trifluoromethanesulfonate as a condensation promotor in the presence of Molecular Sieve to give p-methoxybenzylglycoside compound (1). This compound is treated with sodium methoxide-methanol to remove acetyl and then reacted with benzaldehydedimethylacetal in the presence of a catalytic amount of p-toluenesulfonic acid to give benzylidene compound (3). Subsequently, using methyl 2,3,4-tribenzyl-1-thio-β-L-fucopyranoside (compound (4)) as a donor, compound (3) is converted to an α-fucosyl-(1→3)-glucosamine derivative (compound (5)).

Reaction Scheme 2
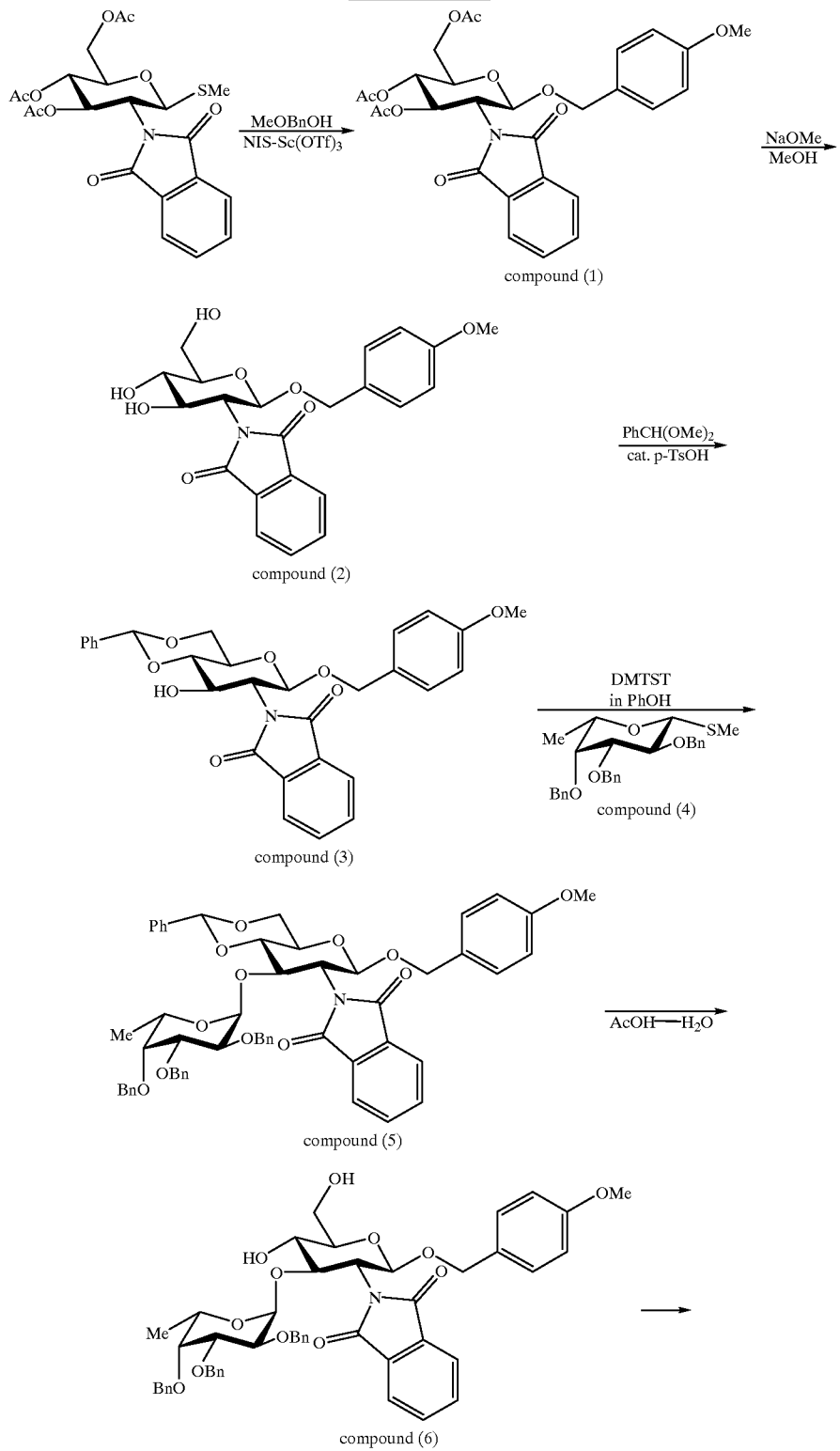

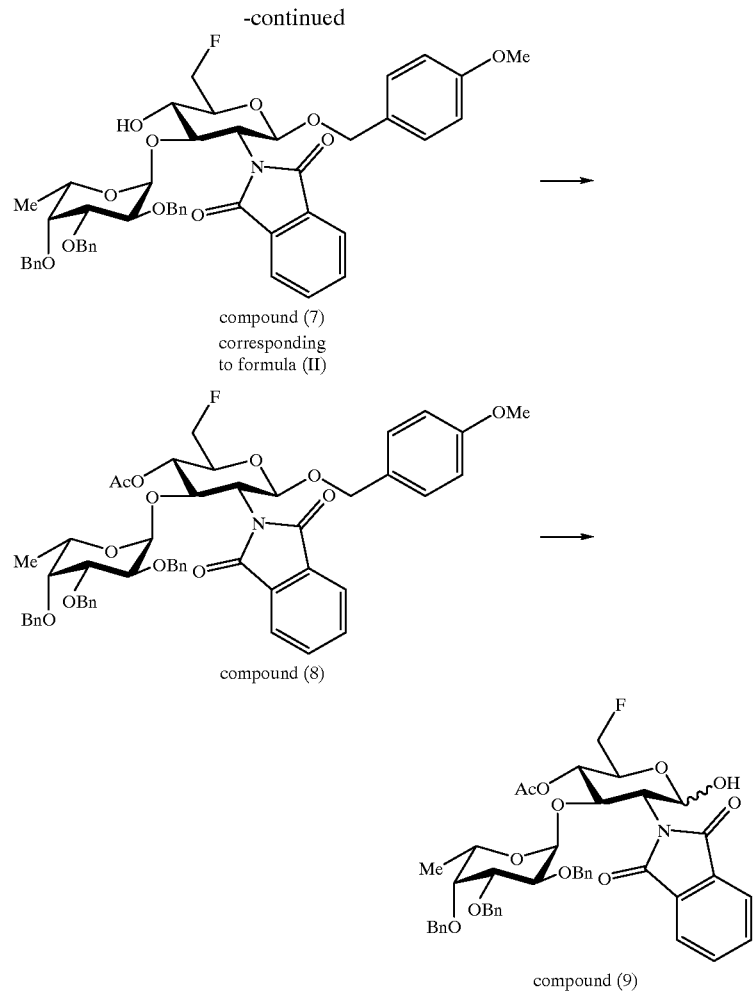

The benzylidene group is removed from compound (5) using acetic acid-water, and the resulting compound (6) is treated with DAST within the temperature range of −45° C. to 0° C. for 4 hours to give compound (7) of formula (II). Secondary alcohol is acetylated with pyridine-acetic anhydride and the resulting compound (8) is treated with trifuloroacetic acid to give de-p-methoxybenzylated compound (9).

From the above compound of formula (II), a sialyl Lewis X sugar chain of formula (I) can be derived according to the reaction steps shown below in Reaction Scheme 3.

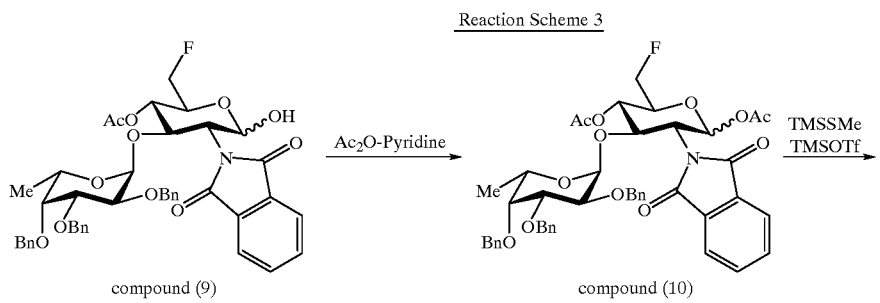

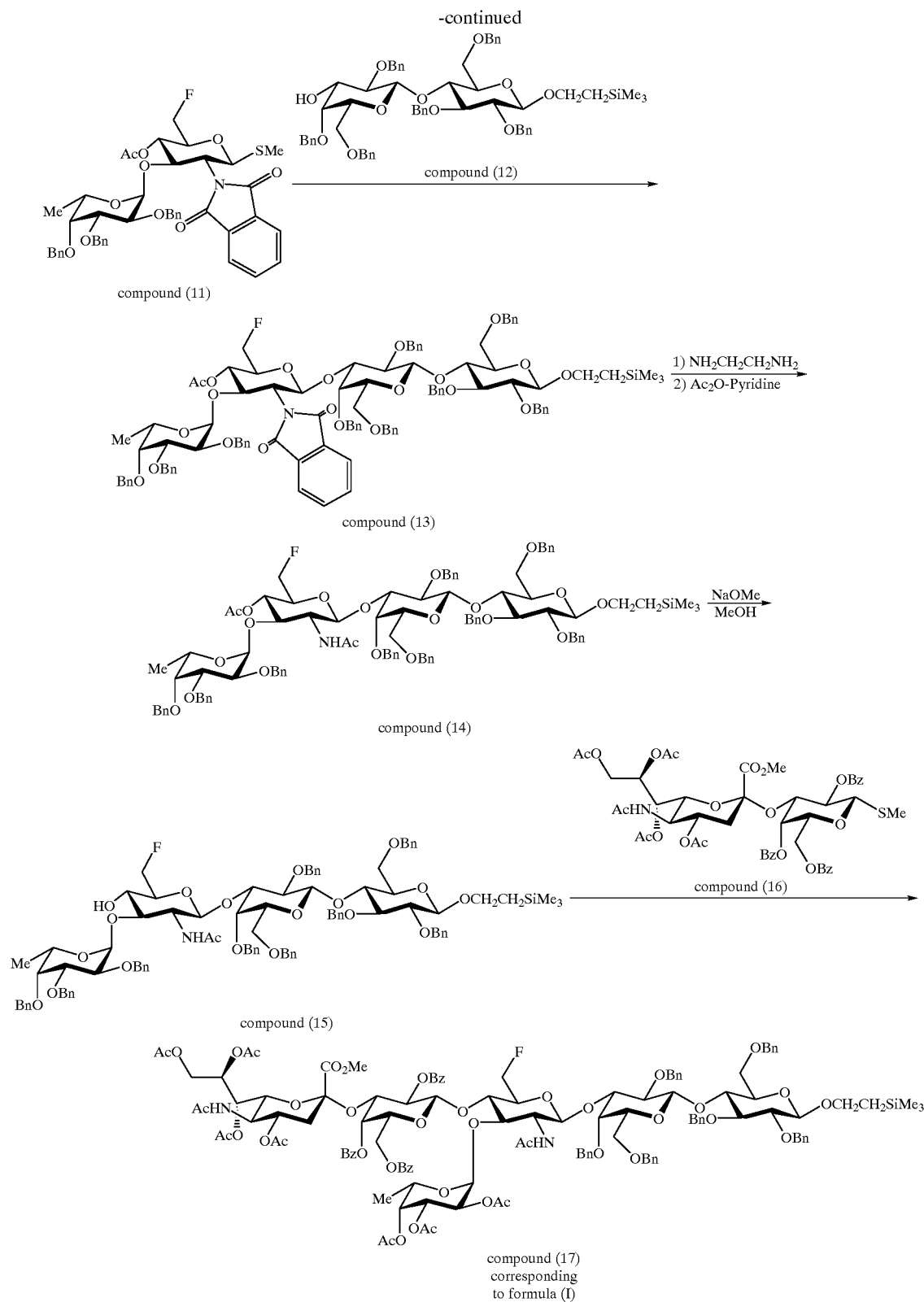

compound (17) corresponding to formula (I)

More specifically, compound (9) is acetylated with acetic anhydride in the presence of an organic base (e.g., pyridine) and the resulting compound (10) is reacted with a Lewis acid (e.g., boron trifluoride-ether complex, trialkylsilyltrifluoromethanesulfonate, etc.) in an inert solvent (e.g., benzene, toluene, methylene chloride or a mixture thereof) in the presence of a suitable methylthioating agent (methylthiotrimethyl-silane) at 40° C. for 24 hours to derive compound (11). The thiomethyl compound is treated with compound (12) in an inert solvent (e.g., benzene, toluene, methylene chloride or a mixture thereof) in the presence of a suitable glycosylation accelerator (e.g., N-iodosuccinimide/scandium trifluoromethanesulfonate, N-iodosuccinimide/tetrabutyl ammonium triflate, dimethyl (methylthio)sulfonium triflate, etc.) at −20° C. to −15° C. for 1 hour to derive compound (13). This compound is converted to compound (14) by removal of phthalimide from the glucosamine portion with ethylenediamine and acetylation with pyridine-acetic anhydride. Then removal of O-acetyl from the glucosamine portion of this compound under alkaline conditions of sodium methoxide-methanol gives compound (15). Since hydroxyl groups are all protected except the hydroxyl group at 4-position of the glucosamine portion, introduction of sialyl galactose (compound (16)) gives compound (17) of formula (I).

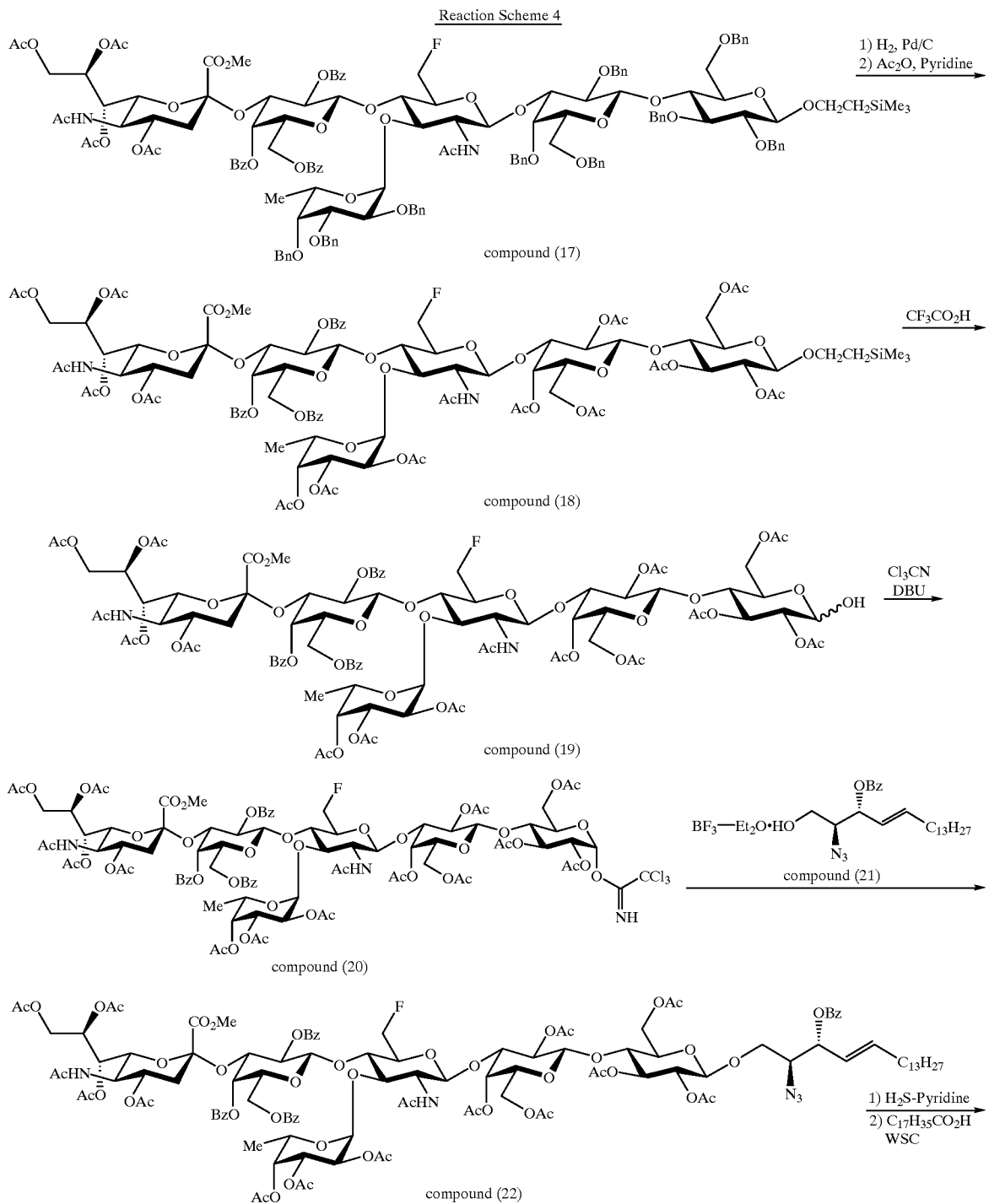

Reaction Scheme 4

-continued

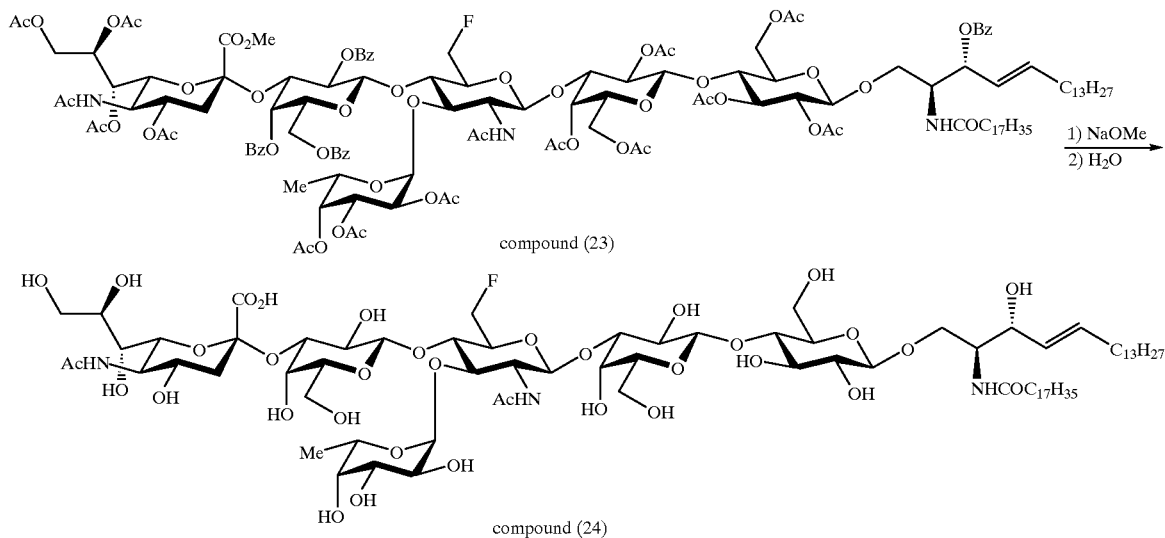

compound (23)

compound (24)

The benzyl group is removed from the obtained sialyl Lewis X sugar chain by catalytic reduction and the resulting free hydroxyl group is acetylated to yield compound (18). Then removal of trimethylsilylethyl at 2-position of glucose by the action of trifluoroacetic acid gives compound (19). This compound is treated with 1,8-diazabicyclo[5.4.0] undeca-7-ene (DBU) and trichloroacetonitrile ($CCl_3CN$) to yield compound (20). Then, the compound is treated with boron trifluoride ether complex in the presence of an azide sphingosine derivative (compound (21)) to give compound (22). The azide group of compound (22) is reduced with hydrogen sulfide gas, followed by condensation with octawater) to give the desired fluorine substituted sialyl Lewis X derivative, compound (24). The reducing agent for use to reduce the azide group is not limited to hydrogen sulfide, but includes any reducing agent which can reduce an azide group, does not reduce a double bond and does not release an acyl protective group. This reaction process is shown in Reaction Scheme 4.

Compound (18) may easily be deprotected under conditions similar to those for synthesis of compound (24). This reaction process is shown in Reaction Scheme 5.

Reaction Scheme 5

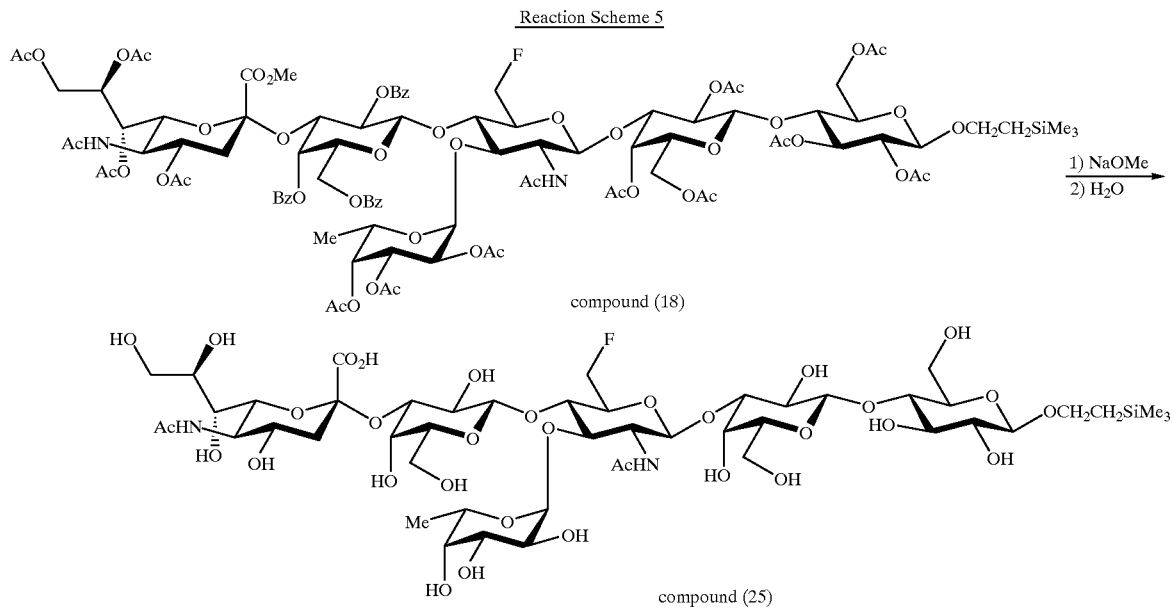

compound (18)

compound (25)

decanoic acid in the presence of a dehydrating condensation agent (e.g., 1-ethyl-3-(3-dimethylaminopropyl) carbodiimide hydrochloride, etc.) to give compound (23). Compound (23) is then deprotected (for example, by treatment with sodium methoxide-methanol and addition of Compound (4) used herein may easily be synthesized according to a method similar to that described in J. Carbohydrate Research, 10, 549–560 (1991). Likewise, compounds (12) and (16) may easily be synthesized according to methods similar to those described in Carbohydrate Research, 200, 269–285 (1990).

Further, compound (21) can be easily obtained according to a method as described in Carbohydrate Research, 202, 177–191 (1990), which comprises synthesizing azide sphingosine, protecting a primary hydroxyl group at 1-position thereof with an appropriate protective group such as triphenylmethyl, protecting hydroxyl at 3-position with benzoyl chloride or the like in a conventional manner and deprotecting 1-position with boron trifluoride-ether complex or the like.

The present inventors further synthesized other Lewis X derivatives by deriving from compound (11) the following compounds (30) to (32) and (34) to (38) of formula (I) according to the reaction steps shown in Reaction Schemes 6 and 7.

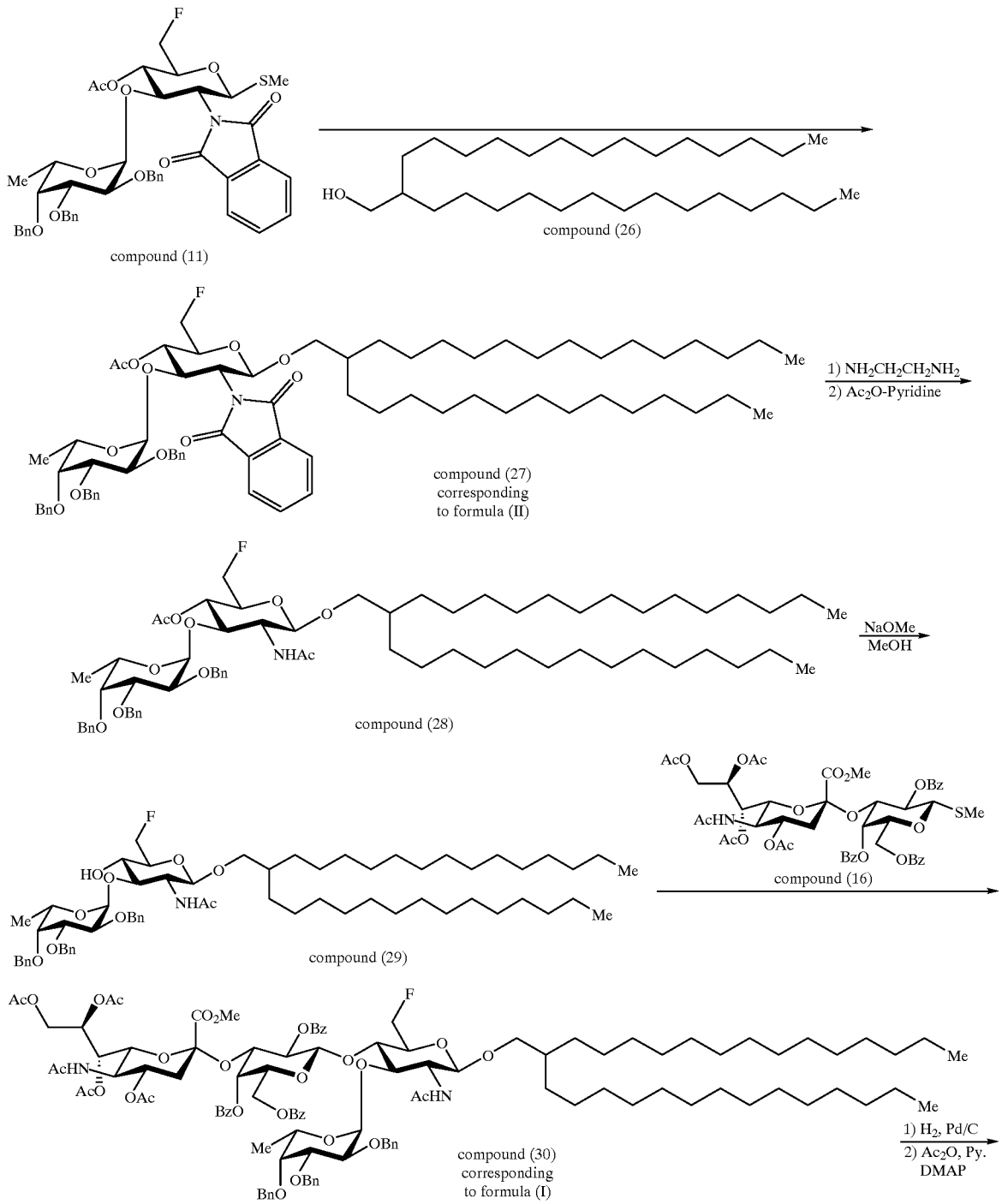

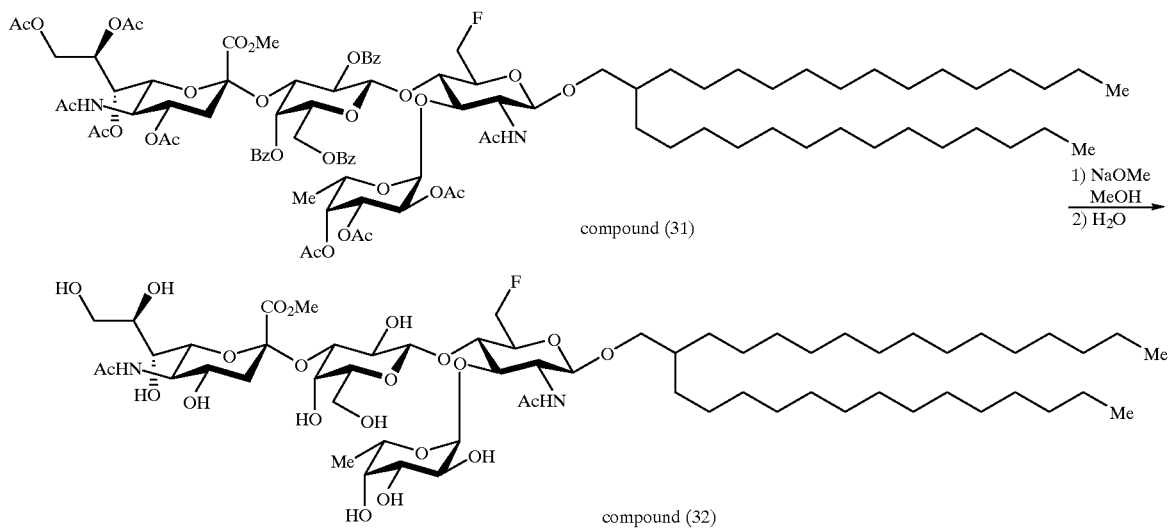

compound (31)

compound (32)

More specifically, compound (11) is treated with compound (26) in an inert solvent (e.g., benzene, toluene, methylene chloride or a mixture thereof) in the presence of an appropriate glycosylation promotor (e.g., N-iodosuccinimide/scandium trifluoromethanesulfonate, N-iodosuccinimide/tetrabutyl ammonium triflate, dimethyl (methylthio)sulfonium triflate, etc.) at $-20°$ C. to $-15°$ C. for 2 hours to derive compound (27) of formula (II) of the invention. Compound (27) is reacted with an excess of ethylenediamine at room temperature to boiling temperature of the solvent for 1 to 48 hours to remove phthalimide from the glucosamine portion and then reacted with an excess of pyridine-acetic anhydride at room temperature for 1 to 24 hours for acelylation. The resulting compound (28) is reacted with a catalytic amount of sodium methoxide-methanol at room temperature for 1 to 12 hours to remove O-acetyl. The resulting compound (29) is reacted with an equimolar to excessive amount of compound (16) in an inert gas atmosphere at room temperature for 1 to 6 hours to give compound (30) of formula (I). Compound (30) is subjected to catalytic reduction in the presence of 10% palladium-carbon at room temperature for 1 to 24 hours to remove benzyl and then reacted with an excess of pyridine-acetic anhydride at room temperature for 1 to 6 hours for acelylation. The resulting compound (31) is reacted with an excess of sodium methoxide-methanol at room temperature for 1 to 24 hours, followed by addition of water to remove protective groups from hydroxyl and carboxylic acid, thus giving the desired fluorine substituted sialyl Lewis X derivative, compound (32).

Reaction Scheme 7

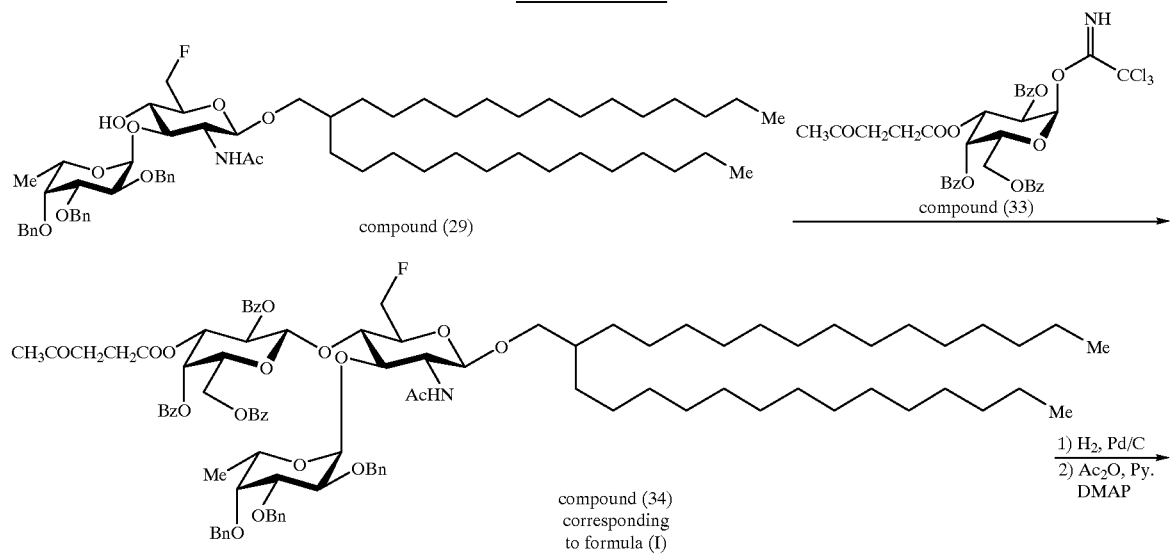

-continued

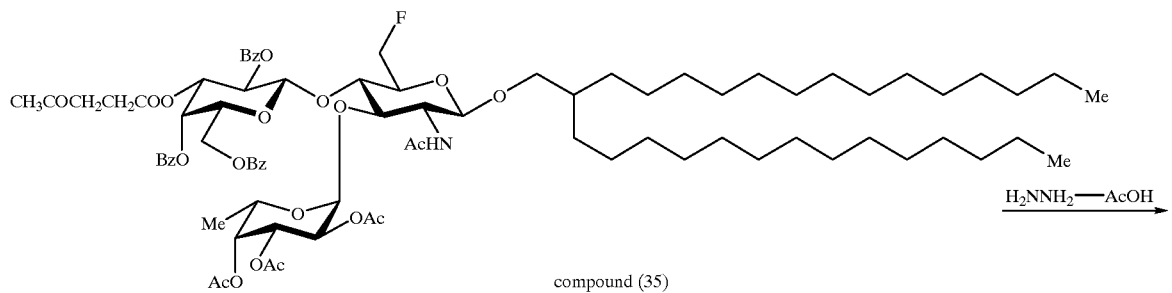
compound (35)

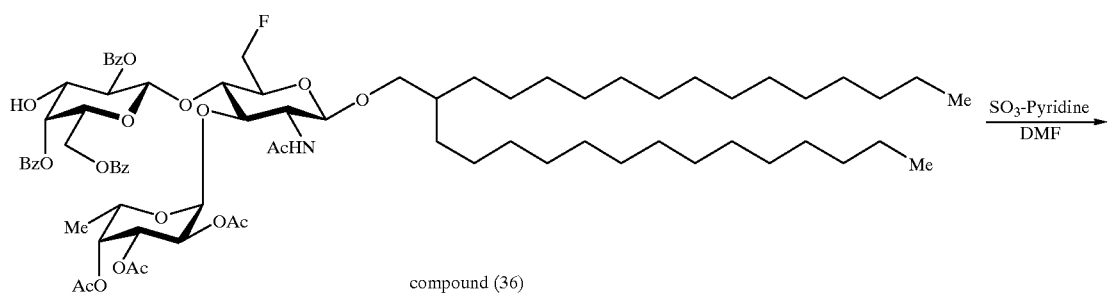
compound (36)

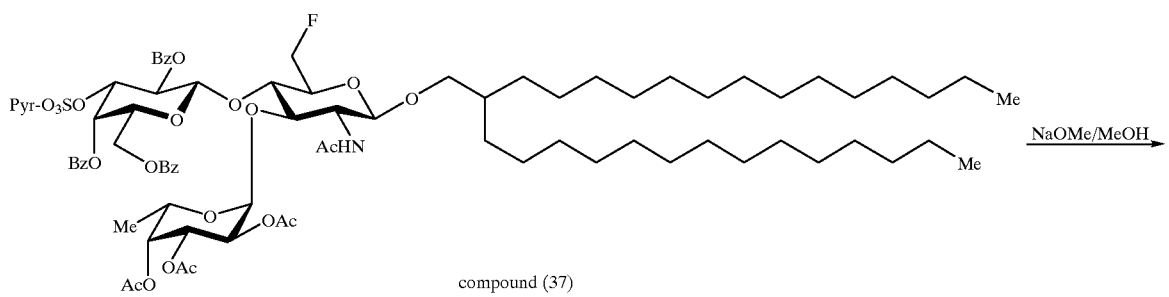
compound (37)

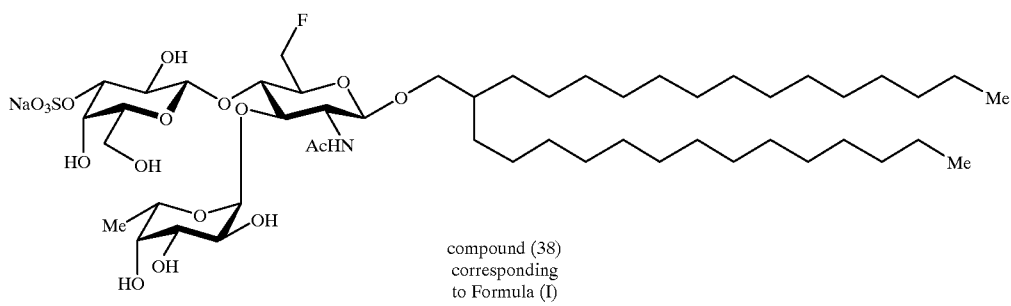
compound (38)
corresponding
to Formula (I)

A Lewis X derivative is derived from compound (29) of formula (II) obtained according to the above-mentioned reaction steps. Compound (29) is treated with a Lewis acid (e.g., boron trifluoride-ether complex, trimethylsilyltrifluoromethanesulfonate, etc.) in the presence of compound (33) to give compound (34) of formula (I). The benzyl group is removed from the Lewis X sugar chain by catalytic reduction and the resulting free hydroxyl group is acetylated. The resulting compound (35) is reacted with hydrazine acetate to give compound (36) of formula (II) having one hydroxyl group. Compound (36) is treated with sulfur trioxide-pyridine complex in the presence of an aprotic solvent (e.g., dimethylformamide, pyridine, dimethyl sulfoxide) for 1 hour to derive compound (37). Finally, removal of the protective groups yields the desired fluorine substituted Lewis X derivative, compound (38).

Compound (26) used herein may easily be synthesized according to the method described in Biochem. Biophys. Res. Commun., 203, 1102–1109 (1994). Also, compound

(33) may easily be synthesized according to the method described in J. Carbohydr. Chem., 14, 369–385 (1995).
The present inventors further derived compound (45) of formula (I) from compound (9) according to the reaction steps shown below in Reaction Scheme 8.
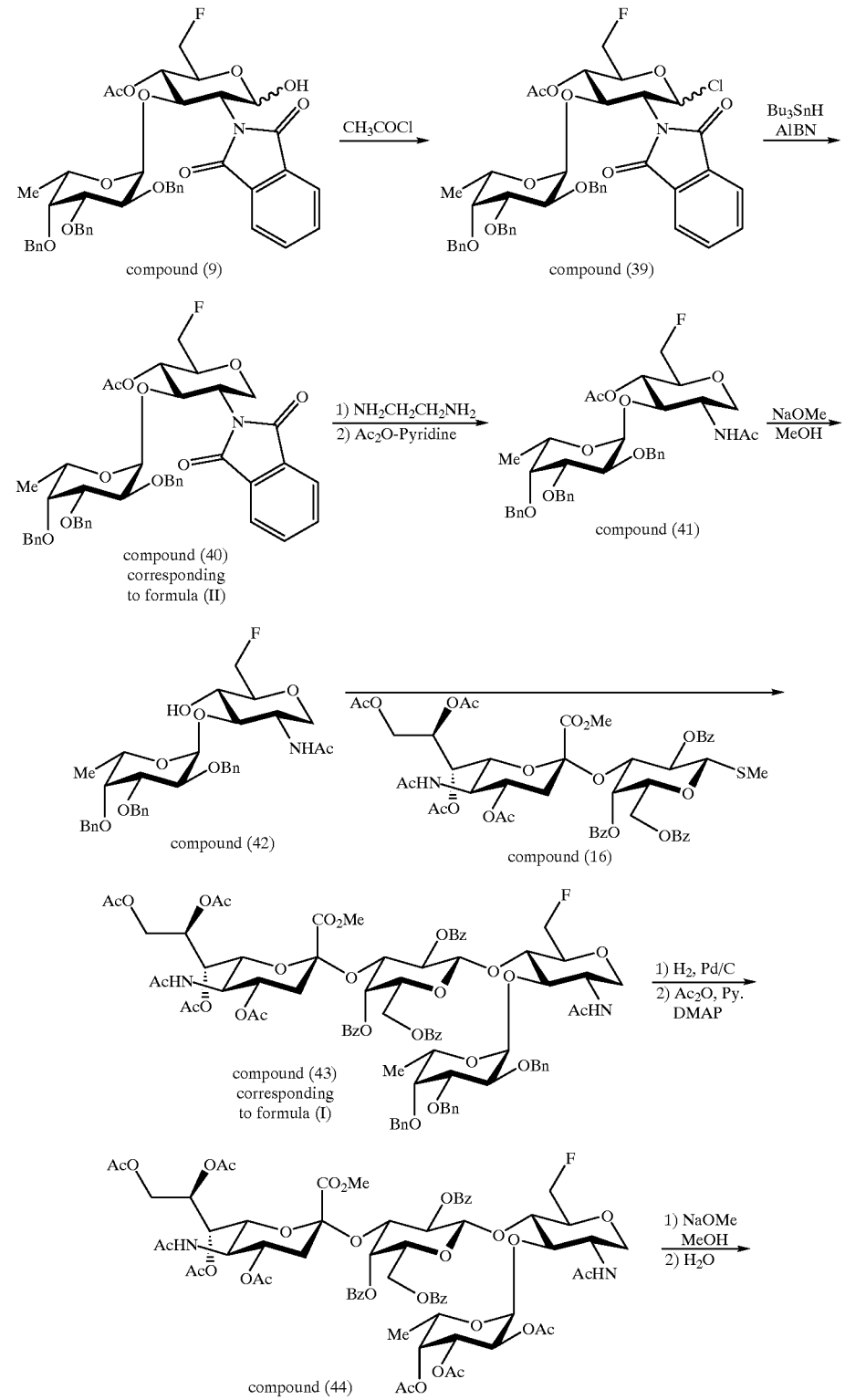
Reaction Scheme 8

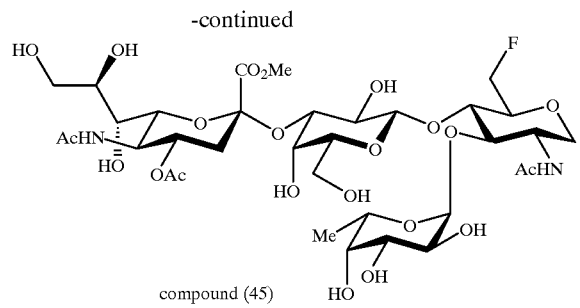

compound (45)

More specifically, compound (9) is treated with acetyl chloride for 16 hours and the resultant crude compound (39) is treated with tributyltin hydride in toluene in the presence of azobisisobutylonitrile to give compound (40) of formula (II). This compound is converted to compound (41) by removal of phthalimide from the glucosamine portion with ethylenediamine and acetylation with pyridine-acetic anhydride. Then removal of O-acetyl from the glucosamine portion of compound (41) under alkaline conditions of sodium methoxide-methanol gives compound (42). Since hydroxyl groups are all protected except the hydroxyl group at 4- position of the glucosamine portion, introduction of sialyl galactose (using compound (16) as a donor) gives compound (43) of formula (I). The benzyl group is removed from the obtained 1-deoxysialyl Lewis X sugar chain by catalytic reduction and the resulting free hydroxyl group is acetylated to give compound (44). Then the protective groups are removed from hydroxyl and carboxyl of compound (44) (for example, by treatment with sodium methoxide-methanol and addition of water) to give the desired fluorine substituted 1-deoxy sialyl Lewis X sugar chain, compound (45).

The compounds of formula (I) of the invention may be produced according to the above Reaction Schemes 1 to 8 but more generally can be obtained according to the following Reaction Scheme 9.

Reaction Scheme 9

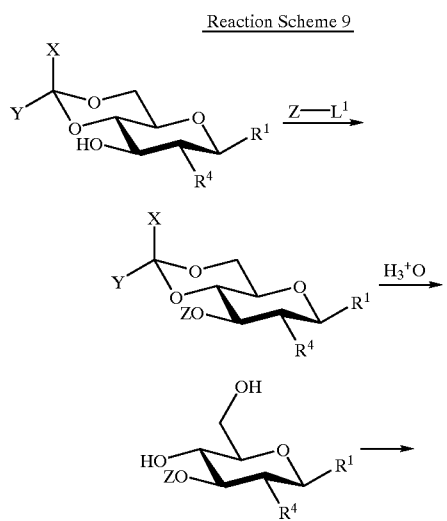

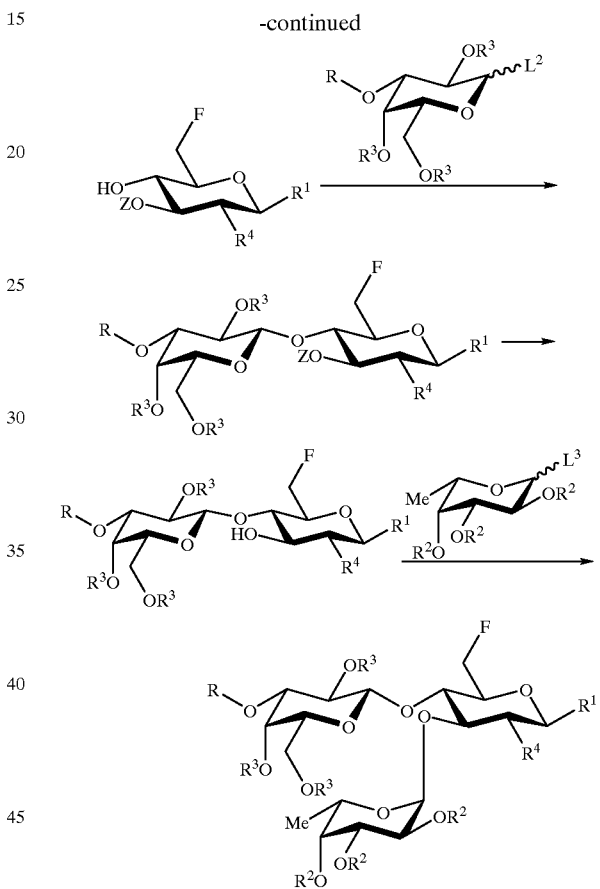

wherein X and Y are the same or different and independently represent hydrogen, lower alkyl, or unsubstituted or substitued phenyl, Z represents p-methoxybenzyl, trimethylsilylethyl, trimethylsilylethoxyethyl, t-butyldimethylsilyl, t-butyldiphenylsilyl or like hydroxyl-protective group. $L^1$ represents an eliminating group, for example, halogen such as iodine, chlorine or bromine, and aliphatic or aromatic sulfonyloxy such as p-toluenesulfonyloxy, chloromethanesulfonyloxy, methanesulfonyloxy or trifluoromethanesulfonyloxy. $L^2$ represents a group conventionally used as an eliminating group of a sugar donor for glycosylation, for example, halogen such as iodine, chlorine, bromine or fluorine; aliphatic or aromatic thio such as methylthio, ethylthio, phenylthio or p-methoxyphenylthio; a phosphorus-containing group such as diphenylphosphate, diphenylphosphineimidate or phosphorodiamideimidethioate; trichloroacetoimidate or 4-pentenyl. $L^3$ represents a group conventionally used as an eliminating group of a sugar donor for glycosylation, for example, halogen such as iodine, chlorine, bromine or fluorine; aliphatic or aromatic thio such as methylthio, ethylthio, phenylthio or p-methoxyphenylthio; a phosphorus-containing group such as diphenylphosphate, diphenylphosphineimidate or phosphorodiamideimidethioate; trichloroacetoimidate or 4-pentenyl.

The reaction conditions for the steps in Reaction Scheme-9 can be easily decided by any person with ordinary skill in the art with reference to Reaction Schemes 1 to 8 and working examples shown below.

The compound wherein R is $PO(OH)_2$ can be prepared from the corresponding compound wherein R is hydroxyl, using o-xylene N,N-diethylphosphor amidide, according to the following Reaction Scheme 10.

Reaction Scheme 10

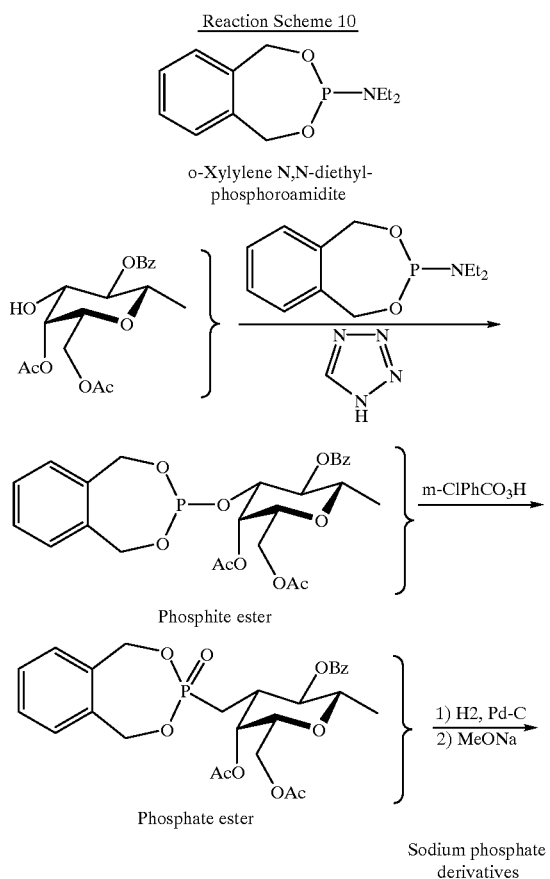

The compounds of the invention may be in the form of salts of an alkali metal such as sodium or potassium. These salts can be formed according to conventional methods.

When used as physiologically active substances against inflammation or inflammation-associated diseases, the compounds of the invention may be made into various dosage forms, for example, tablets, capsules, granules, fine particles, powders or like oral preparations, injections, suppositories, ointments, creams, inhalants, nasal sprays, lotions or the like. Such preparations can be formulated by methods already known and conventional to those skilled in the art.

Solid medicine for oral administration can be prepared by adding to the compound of the invention excipients, binders, disintegrators, lubricants, coloring agents, flavors or the like and forming them into tablets, granules, powders, capsules or the like in a conventional manner. Such additives for use may be selected from those conventionally used in this technical field. Examples of useful excipients are lactose, sucrose, sodium chloride, glucose, starch, calcium carbonate, kaolin, crystalline cellulose, silicic acid and the like; useful binders are water, ethanol, propanol, simple syrup, glucose solution, starch solution, gelatin solution, carboxymethyl cellulose, carboxypropyl cellulose, hydroxypropylstarch, methyl cellulose, ethyl cellulose, shellac, calcium phosphate, polyvinyl pyrrolidone and the like; useful disintegrators are dried starch, sodium alginate, agar powder, sodium hydrogencarbonate, calcium carbonate, sodium lauryl sulfate, stearic acid monoglyceride, lactose and the like; useful lubricants are purified talc, stearic acid salt, borax, polyethylene glycol and the like; and useful flavors are sucrose, bitter orange peel, tartaric acid and the like.

Liquid medicine for oral administration can be prepared by adding to the compound of the invention flavors, buffers (e.g., sodium citrate), stabilizers (e.g., tragacanth, gum arabic, gelatine, etc.) or the like and forming them into liquids for internal use, syrups, elixirs or the like in a conventional manner.

Injections can be prepared by adding to the compound of the invention pH adjusters, buffers, stabilizers, isotonizing agents, local analgesics or the like and forming them into subcutaneous, intramuscular or intravenous injections in a conventional manner. Examples of useful pH adjusters and buffers are sodium citrate, sodium acetate, sodium phosphate and the like. Examples of useful stabilizers are sodium pyrosulfite, EDTA, thioglycollic acid, thiolactic acid and the like. Examples of useful local analgesics are procaine hydrochloride, lidocaine hydrochloride and the like.

Suppositories can be prepared by adding to the compound of the invention carriers known in this technical field, for example, polyethyleneglycol, lanolin, cacao butter, fatty acid triglyceride and the like, optionally with surfactants such as Tween (registered trademark) and forming them into suppositories in a conventional manner.

Preferably, the compounds of the invention are administered intravenously. A therapeutically effective amount thereof varies with the severity of disease, body weight and overall condition of the patient. Generally, the daily dosage ranges from about 5 to 500 mg per adult and this amount can be administered once or in 2–4 divided doses.

The present invention is now illustrated by means of the following working examples but these examples in no way are meant to restrict the scope of the invention.

BEST MODE FOR CARRYING OUT THE INVENTION

EXAMPLE 1

Synthesis of 4-Methoxyphenylmethyl 3,4,6-tri-O-acetyl-2-deoxy-2-phthalimide-β-D-glucopyranoside (Hereinafter Referred to as Compound (1))

0.124 g (0.266 mmol) of methyl 3,4,6-tri-O-acetyl-2-deoxy-2-phthalimide-1-thio-β-D-glucopyranoside was dissolved in 4 ml of dichloroethane. Added to the solution under argon atmosphere were 80 µl (0.642 mmol) of 4-methoxybenzyl alcohol and 1.2 g of Molecular Sieve (4 Å). The mixture was cooled to −30° C. and 0.21 g (0.933 mmol) of N-iodosuccinimide and then 46 mg (0.09 mmol) of scandium trifluoromethanesulfonate were added, followed by stirring at −30 to 0° C. for 2 hours. The mixture was again cooled to −30° C. and 0.9 mol of methanol and 0.3 mol of triethylamine were added, followed by stirring at 0° C. for 30 minutes. The mixture was filtrated through Celite and the Celite was washed with dichloromethane. The filtrate and washing liquids were combined, washed with cooling water and dried over sodium sulfate. After concentration under reduced pressure, the residue was subjected to silica gel flash chromatography (eluent; n-hexane:ethyl acetate=2:1) to give compound (1) (63 mg, 42.6%) and the starting methyl 3,4,6-tri-O-acetyl-2-deoxy-2-phthalimide-1-thio-β-D-glucopyranoside (40 mg, 32.3%).

m.p.: 143–145° C. $C_{28}H_{29}O_{11}N$ (555.54) $[\alpha]_D^{25}$=–5.7° (c=1.01, chloroform)

IR(KBr) νmax $cm^{-1}$: 1750, 1250(ester), 1710(imide), 1080(ether), 720(Ph).

$^1$H-NMR (CDCl$_3$; TMS): δ 8.0–7.6(m, 4H, Phthal), 7.1–6.5(ABq, 4H, MPM), 5.80(dd, 1H, $J_{5,4}$=11.0 Hz, $J_{4,3}$=9.1 Hz, H-4), 5.35(d, 1H, $J_{1,2}$=8.5 Hz, H-1), 5.20(dd, 1H, $J_{3,2}$=9.1 Hz, $J_{4,3}$=9.1 Hz, H-3), 4.62(ABq, 2H, CH$_2$PhOMe), 3.71(s, 3H, CH$_3$O), 2.14, 2.03, 1.85(3s, 9H, 3AcO).

Mass spectrometry: m/z for $C_{28}H_{30}NO_{11}$ Calculated: 556.1819 (M+H); Found: 556.1804

EXAMPLE 2

Synthesis of 2,4-Methoxyphenylmethyl 4,6-O-benzylidene-2-deoxy-2-phthalimide-β-D-glucopyranoside (Hereinafter Referred to as Compound (3))

0.810 g (1.46 mmol) of compound (1) was dissolved in 18 ml of absolute methanol. Under argon atmosphere, 30 mg of sodium methoxide was added and the mixture was stirred at room temperature for 2.5 hours. The reaction mixture was directly passed through a column of Amberlite IR120B(H$^+$) (eluent: methanol) for neutralization and the eluate was collected and concentrated under reduced pressure. The resultant crude compound (2) (642 mg) was dissolved in 6 ml of anhydrous dimethylformamide and then 1.4 ml (9.33 ml) of benzaldehydedimethylacetal and 2.6 ml (0.14 mmol) of p-toluenesulfonic acid monohydrate were added under argon atmosphere, followed by stirring at room temperature for 16 hours. The reaction mixture was passed through a column of Amberlite IRA-410(OH$^-$)(eluent: methanol) and the eluate was collected and concentrated under reduced pressure. The residue was purified by silica gel flash chromatography (hexane:ethyl acetate=3:2) to give compound (3) (626 mg, 80.9%). $C_{29}H_{27}NO_8$ (517.54)

$^1$H-NMR (CDCl$_3$; TMS): δ 7.9–7.3(m, 9H, Phthal+Ph), 7.1–6.4(ABq, 4H, MPM), 5.58(s, 1H, PhCH), 5.26(d, 1H, $J_{1,2}$=8.5 Hz, H-1), 4.61(ABq, 2H, CH$_2$PhOMe), 3.69(s, 3H, CH$_3$O).

Mass spectrometry: m/z for $C_{29}H_{28}NO_8$ Calculated: 518.1815 (M+H); Found: 518.1827

EXAMPLE 3

Synthesis of 4-Methoxyphenylmethyl O-(2,3,4-tri-O-benzyl-α-L-fucopyranosyl)-(1→3)-4,6-O-benzylidene-2-deoxy-2-phthalimide-β-D-glucopyranoside (Hereinafter Referred to as Compound (5))

0.330 g (0.638 mmol) of compound (3) and 0.393 g (0.846 mmol) of methyl 2,3,4-tri-O-benzyl-1-thio-β-L-fucopyranoside compound (4) were dissolved in 12 ml of anhydrous benzene. Under argon atmosphere, 1.2 g of Molecular Sieve (4 Å) was added and the mixture was stirred at room temperature for 2 hours. After cooling to about 7° C., 0.497 g (2.21 mmol) of N-iodosuccinimide and 0.11 g (0.224 mmol) of scandium trifluoromethanesulfonate were added and the mixture was stirred at the same temperature for 10 minutes. After cooling to 4° C., 2.3 ml of methanol and then 0.75 ml of triethylamine were added and the mixture was stirred at the same temperature for 30 minutes. Insoluble materials were suction filtrated out and washed with dichloromethane. The filtrate and washing liquids were combined, washed with water, dried over magnesium sulfate and concentrated under reduced pressure. The residue was purified by flash chromatography (eluent; n-hexane:ethyl acetate=3:1) to give compound (5) (523 mg, 87.8%). $C_{56}H_{55}NO_{12}$ (934.05) $[\alpha]_D^{25}$=34.9° (c=1.00, chloroform)

IR(KBr) νmax $cm^{-1}$: 1720(imide), 1100(ether), 720, 700 (Ph).

$^1$H-NMR (CDCl$_3$; TMS): δ 7.9–6.4(m, 28H, Phthal+4Ph+MPM), 5.56(s, 1H, PhCH), 5.32(d, 1H, $J_{1,2}$=8.5 Hz, H-1, glucosamine portion), 4.61(ABq, 2H, CH$_2$PhOMe), 3.67(s, 3H, CH$_3$O), 0.85(d, 3H, $J_{5,6}$=6.6 Hz, H-6, fucose portion).

Mass spectrometry: m/z for $C_{56}H_{55}NO_{12}Na$ Calculated: 956.3622 (M+Na); Found: 956.3600

EXAMPLE 4

Synthesis of 4-Methoxyphenylmethyl O-(2,3,4-tri-O-benzyl-α-L-fucopyranosyl)-(1→3)-2-deoxy-2-phthalimide-β-D-glucopyranoside (Hereinafter Referred to as Compound (6))

0.410 g (0.439 mmol) of compound (5) was dissolved in 34 ml of 79% acetic acid aqueous solution, followed by stirring at 60° C. for 24 hours. The solvent was concentrated at temperatures not higher than 50° C., and the residue was purified by flash chromatography (eluent; n-hexane:ethyl acetate=1:1) to give compound (6) (235 mg, 63.3%). $C_{49}H_{51}NO_{12}$ (845.94) $[\alpha]_D^{24}$=+14.7° (c=0.52, chloroform)

IR(KBr) νmax $cm^{-1}$: 3500(OH), 1720(imide), 1070 (ether), 720, 700(Ph).

$^1$H-NMR (CDCl$_3$; TMS): δ 7.9–6.4(m, 23H, Phthal+3Ph+MPM), 5.38(d, 1H, $J_{1,2}$=8.4 Hz, H-1, glucosamine portion), 4.61(ABq, 2H, CH$_2$PhOMe), 4.59(d, 1H, $J_{1,2}$=3.3 Hz, H-1, fucose portion), 3.72(s, 3H, CH$_3$O), 1.06(d, 3H, $J_{5,6}$=6.5 Hz, H-6, fucose portion).

Mass spectrometry: m/z for $C_{49}H_{51}NO_{12}Na$ Calculated: 868.3309 (M+Na); Found: 868.3296

EXAMPLE 5

Synthesis of 4-Methoxyphenylmethyl O-(2,3,4-tri-O-benzyl-α-L-fucopyranosyl)-(1→3)-2,6-dideoxy-6-fluoro-2-phthalimide-β-D-glucopyranoside (Hereinafter Referred to as Compound (7))

50.0 mg (0.059 mmol) of compound (6) was dissolved in 5 ml of anhydrous dichloromethane under argon atmosphere. The solution was cooled to –40° C. and 150 μl (1.44 mmol) of diethylaminosulfur trifluoride (DAST) was added. The mixture was heated for 30 minutes to –20° C. and then stirred at –20 to 0° C. for 2 hours. The mixture was cooled again to –40° C. and 1.9 ml of methanol and then 190 mg of sodium hydrogencarbonate were added thereto with stirring, followed by heating for 1 hour to room temperature. After concentration under reduced pressure, the residue was purified by flash chromatography (eluent; n-hexane:ethyl acetate=3:1) to give compound (7) (35.8 mg, 71.4%). $C_{49}H_{50}NO_{11}F$ (847.93) IR(KBr) νmax $cm^{-1}$: 3400(OH), 1720(imide), 1100(ether) 720, 700(Ph).

$^1$H-NMR (CDCl$_3$; TMS): δ 7.9–6.4(m, 23H, Phthal+3Ph+MPM), 5.35(d, 1H, $J_{1,2}$=8.4 Hz, H-1, glucosamine portion), 3.72(s, 3H, CH$_3$O), 1.06(d, 3H, $J_{5,6}$=6.5 Hz, H-6, fucose portion).

$^{19}$F-NMR (CDCl$_3$; CFCl$_3$): δ –234(dt, JF,6H=47 Hz, JF,5H=23 Hz, 6-F, glucosamine portion).

Mass spectrometry: m/z for $C_{49}H_{50}NO_{11}FNa$ Calculated: 870.3266 (M+Na); Found: 870.3237

EXAMPLE 6

Synthesis of 4-Methoxyphenylmethyl O-(2,3,4-tri-O-benzyl-α-L-fucopyranosyl)-(1→3)-4-O-acetyl-2,6dideoxy-6-fluoro-2-phthalimide-β-D-glucopyranoside (Hereinafter Referred to as Compound (8))

220 mg (0.142 mmol) of compound (7) was dissolved in 6 ml of pyridine under argon atmosphere. The solution was cooled to 0° C. and 3.3 ml of acetic anhydride was added. The mixture was heated to room temperature and stirred for 24 hours. After concentration under reduced pressure, the residue was purified by flash chromatography (eluent; n-hexane:ethyl acetate=3:1) to give compound (8) (224 mg, 97.0%). $C_{51}H_{52}NO_{12}F$ (889.97) $[\alpha]_D^{23}$=+22.1° (c=0.52, chloroform)

IR(KBr) νmax cm$^{-1}$: 1750, 1230(ester), 1720(imide), 1080(ether), 720, 700(Ph).

$^1$H-NMR (CDCl$_3$; TMS): δ 7.9–6.4(m, 23H, Phthal+3Ph+MPM), 5.40(d, 1H, $J_{1,2}$=8.4 Hz, H-1, glucosamine portion), 3.71(s, 3H, CH$_3$O), 1.98(s, 3H, COCH$_3$), 0.95(d, 3H, $J_{5,6}$=6.5 Hz, H-6, fucose portion).

$^{19}$F-NMR (CDCl$_3$; CFCl$_3$): δ −230(dt, JF,6H=47 Hz, JF,5H=19 Hz, 6-F, glucosamine portion).

Mass spectrometry: m/z for $C_{51}H_{52}NO_2FNa$ Calculated: 912.3372 (M+Na); Found: 912.3361

EXAMPLE 7
Synthesis of O-(2,3,4-Tri-O-benzyl-α-L-fucopyranosyl)-(1→3)-4-O-acetyl-2,6-dideoxy-6-fluoro-2-phthalimide-D-glucopyranoside (Hereinafter Referred to as Compound (9))

208 mg (0.234 mmol) of compound (8) was dissolved in 14 ml of 10% trifluoroacetic acid-dichloromethane solution at 0° C. After stirring under argon atmosphere at the same temperature for 2 hours, the reaction mixture was poured into 280 ml of saturated sodium hydrogencarbonate aqueous solution as cooled with ice. The mixture was extracted with ethyl acetate three times and dried over sodium sulfate. After concentration under reduced pressure, the residue was purified by flash chromatography (eluent; n-hexane:ethyl acetate-=2:1) to give compound (9) (180 mg, 100%). $C_{43}H_{44}NO_{11}F$ (769.82)

$^1$H-NMR (CDCl$_3$; TMS): δ 7.9–6.9(m, 19H, Phthal+3Ph), 5.7(m, 1H, H-1, glucosamine portion), 2.00(s, 3H, COCH$_3$), 0.96(d, 3H, $J_{5,6}$=6.5 Hz, H-6, fucose portion).

$^{19}$F-NMR (CDCl$_3$; CFCl$_3$): δ −230 (dt, 0.92F, JF,6H=48 Hz, JF,5H=19 Hz, 6-F, β-glucosamine portion), −232(dt, 0.08F, JF,6H=48 Hz, JF,5H=24 Hz, 6-F, α-glucosamine portion).

EXAMPLE 8
Synthesis of O-(2,3,4-Tri-O-benzyl-α-L-fucopyranosyl)-(1→3)-1,4-di-O-acetyl-2,6-dideoxy-6-fluoro-2-phthalimide-D-glucopyranoside (Hereinafter Referred to as Compound (10))

180 mg (0.234 mmol) of compound (9) was dissolved in 6 ml of anhydrous pyridine under argon atmosphere. The solution was cooled to 0° C. and 3.0 ml of acetic anhydride was added. The mixture was heated to room temperature and stirred at room temperature for 24 hours. The reaction mixture was concentrated under reduced pressure and the residue was purified by flash chromatography (eluent; n-hexane:ethyl acetate=3:1) to give compound (10) (185 mg, 97.5%). $C_{45}H_{46}NO_{12}F$ (811.86)

IR(KBr) νmax cm$^{-1}$: 1760, 1220(ester), 1720(imide), 1090(ether), 720, 700(Ph).

$^1$H-NMR (CDCl$_3$; TMS): δ 7.9–6.9(m, 19H, Phthal+3Ph), 6.58(d, 0.94H, $J_{1,2}$=8.9 Hz, H-1, β-glucosamine portion), 6.36(d, 0.06H, $J_{1,2}$=4.0 Hz, H-1, α-glucosamine portion), 2.03, 2.01(2s, 6H, 2COCH$_3$), 0.97(d, 3H, $J_{5,6}$=6.5 Hz, H-6, fucose portion).

$^{19}$F-NMR (CDCl$_3$; CFCl$_3$): δ −232 (dt, 0.94F, JF,6H=47 Hz, JF,5H=12 Hz, 6-F, β-glucosamine portion), −231 (dt, 0.06F, JF,6H=47 Hz, JF,5H=21 Hz, 6-F, α-glucosamine portion).

Mass spectrometry: m/z for $C_{45}H_{46}NO_{12}FNa$ Calculated: 834.2902 (M+Na); Found: 834.2877

EXAMPLE 9
Synthesis of O-(2,3,4-Tri-O-benzyl-α-L-fucopyranosyl)-(1→3)-4-O-acetyl-2,6-dideoxy-6-fluoro-2-phthalimide-1-thio-β-D-glucopyranoside (Hereinafter Referred to as Compound (11))

63 mg (0.018 mmol) of compound (10) was dissolved in 1 ml of anhydrous dichloroethane under argon atmosphere. Thereto were added 0.1 ml (0.71 mmol) of (methylthio)trimethylsilane and then 14 ml (0.072 mmol) of trimethylsilyl trifluoromethanesulfonate, followed by stirring at 35° C. for 12 hours. The reaction mixture was allowed to cool and diluted with dichloromethane. The mixture was washed with 1M sodium hydrogencarbonate aqueous solution and then with saturated sodium chloride aqueous solution and dried over sodium sulfate. After concentration under reduced pressure, the residue was purified by flash chromatography (eluent; n-hexane:ethyl acetate=3:1) to give compound (11) (49 mg, 79.0%). $C_{44}H_{46}NO_{10}FS$ (799.91)

$^1$H-NMR (CDCl$_3$; TMS): δ 7.9–6.9(m, 19H, Phthal+3Ph), 5.42(d, H, $J_{1,2}$=10.3 Hz, H-1, β-glucosamine portion), 4.57 (d, 1H, $J_{1,2}$=3.2 Hz, H-1, fucose portion), 2.19(s, 3H, SCH$_3$), 2.00(s, 3H, COCH$_3$), 0.96(d, 3H, $J_{5,6}$=6.5 Hz, H-6, fucose portion).

$^{19}$F-NMR (CDCl$_3$; CFCl$_3$): δ −232(dt, JF,6H=47 Hz, JF,5H=20 Hz, 6-F, β-glucosamine portion).

EXAMPLE 10
Synthesis of 2-(Trimethylsilyl)ethyl O-(2,3,4-tri-O-benzyl-α-L-fucopyranosyl)-(1→3)-O-(4-O-acetyl-2,6-dideoxy-6-fluoro-2-phthalimide-β-D-glucopyranosyl-(1→3)-O-(2,4,6-tri-O-benzyl-β-D-galactopyranosyl)(1→4)-2,3,6-tri-O-benzyl-β-D-glucopyranoside (Hereinafter Referred to as Compound (13))

37 mg (0.046 mmol) of compound (11) and 45 mg (0.046 mmol) of 2-(trimethylsilyl)ethyl O-(2,4,6-tri-O-benzyl-β-D-galactopyranosyl)-(1→4)(2,3,6-tri-O-benzyl-β-D-glucopyranoside compound (12) were dissolved in 2 ml of anhydrous dichloromethane. Under argon atmosphere, 0.2 g of Molecular Sieve (4 Å) was added and the mixture was stirred at room temperature for 11 hours. After cooling to −20° C., 56 mg (0.25 mmol) of N-iodosuccinimide and then 10 mg (0.02 mmol) of scandium trifluoromethanesulfonate were added and the mixture was stirred at −20 to −15° C. for 50 minutes. The reaction mixture was diluted with dichloromethane and filtrated through Celite, followed by washing with dichloromethane. The filtrate and washing liquids were combined, washed with 1M sodium hydrogencarbonate aqueous solution and then with saturated sodium chloride aqueous solution, and dried over sodium sulfate. After concentration under reduced pressure, the residue was purified by flash chromatography (eluent; n-hexane:ethyl acetate=3:1) to give compound (13) (41 mg, 51.2%). $C_{102}H_{112}NO_{21}FSi$ (1735.09) $[\alpha]_D^{24}$=+11.2° (c=0.93, chloroform)

IR(KBr) νmax cm$^{-1}$: 1750, 1230(ester), 1720(imide), 1080(ether), 860, 840(Me$_3$Si), 740(Ph).

$^1$H-NMR (CDCl$_3$; TMS): δ 7.9–6.8(m, 49H, Phthal+9Ph), 5.66(d, H, $J_{1,2}$=8.4 Hz, H-1, β-glucosamine portion), 2.02(s, 3H, COCH$_3$), 1.00(m, 2H, CH$_2$SiMe$_3$), 0.96(d, 3H, $J_{5,6}$=6.5 Hz, H-6, fucose portion).

$^{19}$F-NMR (CDCl$_3$; CFCl$_3$): δ −230(dt, JF,6H=47 Hz, JF,5H=19 Hz, 6-F, β-glucosamine portion).

Mass spectrometry: m/z for $C_{101}{}^{13}C_1H_{112}NO_{21}FSiNa$ Calculated: 1757.7412 (M+Na); Found: 1757.7460

EXAMPLE 11
Synthesis of 2-(Trimethylsilyl)ethyl O-(2,3,4-tri-O-benzyl-α-L-fucopyranosyl)-(1→3)-O-(2-acetamide-4-O-acetyl-2, 6-dideoxy-6-fluoro-β-D-glucopyranosyl-(1→3)-O-(2,4,6-tri-O-benzyl-β-D-galactopyranosyl) (1→4)-2,3,6-tri-O-benzyl-β-D-glucopyranoside (Hereinafter Referred to as Compound (14))

114 mg (0.0657 mmol) of compound (13) was dissolved in 9 ml of n-butanol under argon atmosphere. After addition of 3 ml of ethylenediamine, the mixture was stirred at 82° C. for 24 hours and then concentrated under reduced pressure at temperatures not higher than 60° C. To the residue were added 16 ml of pyridine and then 9 ml of acetic anhydride, followed by stirring at room temperature for 16 hours. After re-concentration under reduced pressure, the residue was purified by flash chromatography (eluent; n-hexane:ethyl acetate=2:1) to give compound (14) (92 mg, 85.0%). $C_{96}H_{112}NO_{20}FSi$ (1647.02)

$^1$H-NMR (CDCl$_3$; TMS): δ 7.4–7.0(m, 45H, 9Ph), 5.36(d, H, $J_{1,2}$=8.4 Hz, H-1, β-glucosamine portion), 2.04(s, 3H, COCH$_3$), 1.37(s, 3H, NAc), 1.03(d, $J_{5,6}$=6.4 Hz, H-6, fucose portion), 1.00(m, 2H, CH$_2$SiMe$_3$).

$^{19}$F-NMR (CDCl$_3$; CFCl$_3$): δ −230 (dt, JF,6H=48 Hz, JF,5H=19 Hz, 6-F, β-glucosamine portion).

Mass spectrometry: m/z for $C_{95}{}^{13}C_1H_{113}NO_{20}Fsi$ Calculated: 1647.7643 (M+H); Found: 1647.7606

EXAMPLE 12

Synthesis of 2-(Trimethylsilyl)ethyl O-(2,3,4-tri-O-benzyl-α-L-fucopyranosyl)-(1→3)-O-(2-acetamide-2,6-dideoxy-6-fluoro-β-D-glucopyranosyl-(1→3)-O-(2,4,6-tri-O-benzyl-β-D-galactopyranosyl)(1→4)-2,3,6-tri-O-benzyl-β-D-glucopyranoside (Hereinafter Referred to as Compound (15))

76 mg (0.046 mmol) of compound (14) was dissolved in 10 ml of absolute methanol. After addition of 12 mg (0.22 mmol) of sodium methoxide, the mixture was stirred at room temperature under argon atmosphere for 6.5 hours and the reaction mixture was neutralized with a column of Amberlite IR120B(H$^+$) (eluent: methanol). The eluate was combined and concentrated under reduced pressure. The residue was purified by flash chromatography (eluent; hexane:ethyl acetate=2:1) to give compound (15) (65 mg, 87.8%). $C_{94}H_{110}NO_{19}FSi$ (1604.99) $[α]_D^{23}$=−19.4° (c=1.00, chloroform)

IR(KBr) νmax cm$^{-1}$: 3700–3200(OH, NH), 1660, 1500 (amide), 1070(ether), 860, 840(Me$_3$Si), 740, 700(Ph).

$^1$H-NMR (CDCl$_3$; TMS): δ 7.5–7.0(m, 45H, 9Ph), 1.30(s, 3H, NAc), 1.14(d, $J_{5,6}$=6.0 Hz, H-6, fucose portion), 1.00(m, 2H, CH$_2$SiMe3).

$^{19}$F-NMR (CDCl$_3$; CFCl$_3$): δ −235(dt, JF,6H=47 Hz, JF,5H=23 Hz, 6-F, β-glucosamine portion).

Mass spectrometry: m/z for $C_{93}{}^{13}C_1H_{111}NO_{19}Fsi$ Calculated: 1605.7537 (M+H); Found: 1605.7599

EXAMPLE 13

Synthesis of 2-(Trimethylsilyl)ethyl O-(methyl 5-acetamide-4,7,8,9-tetra-O-acetyl-3,5-dideoxy-D-glycero-α-D-galacto-2-nonulopyranosylonate)-(2→3)-O-(2,4,6-tri-O-benzoyl-β-D-galactopyranosyl-(1→4)-O-[(2,3,4-tri-O-benzyl-α-L-fucopyranosyl)-(1→3)]-O-(2-acetamide-2,6-dideoxy-6-fluoro-β-D-glucopyranosyl-(1→3)-O-(2,4,6-tri-O-benzyl-β-D-galactopyranosyl)-(1→4)-2,3,6-tri-O-benzyl-β-D-glucopyranoside (Hereinafter Referred to as Compound (17))

93 mg (0.058 mmol) of compound (15) and 183 mg (0.183 mmol) of methyl O-(methyl 5-acetamide-4,7,8,9-tetra-O-acetyl-3,5-dideoxy-D-glycero-α-D-galacto-2-nonulopyranosylonate)-(2→3)-2,4,6-tri-O-benzoyl-1-thio-β-D-glucopyranoside (compound (16)) were dissolved in 2 ml of anhydrous dichloromethane under argon atmosphere and 140 mg of activated Molecular Sieve (4 Å) was added. The mixture was stirred at room temperature for 3.5 hours and then a mixture of 70 mg (0.27 mmol) of dimethyl (methylthio)sulfonium triflate (DMTST) and 70 mg of activated Molecular Sieve (4 Å) was added at the same temperature, followed by stirring at the same temperature for 22 hours. The mixture was cooled with ice and 0.36 ml of methanol and 0.18 ml of triethylamine were added, followed by stirring at the same temperature for 30 minutes. After dilution with dichloromethane, insoluble materials were filtered out, followed by washing. The filtrate and washing liquids were combined, washed with water and dried over sodium sulfate. After concentration under reduced pressure, the residue was purified by flash chromatography (eluent; n-hexane:ethyl acetate=1:3) to give compound (17) (39 mg, 26.4%). $C_{141}H_{159}N_2O_{39}Fsi$ (2552.9) $[α]_D^{24}$=−20.8° (c=1.00, chloroform)

IR(KBr) νmax cm$^{-1}$: 3400(NH), 1740, 1270(ester), 1690, 1500(amide), 1070(ether), 860, 840(Me$_3$Si), 740, 710(Ph).

$^1$H-NMR (CDCl$_3$; TMS): δ 8.3–7.0(m, 60H, 12Ph), 5.67 (m, 1H, H-8, sialic acid portion), 5.43(dd, 1H, $J_{1,2}$=8.2 Hz, $J_{2,3}$=9.9 Hz, H-2, galactose portion), 5.30(broad d, 1H, $J_{3,4}$=$J_{4,5}$=3.5 Hz, H-4, galactose portion), 5.23(dd, 1H, $J_{7,8}$=12.4 Hz, $J_{6,7}$=2.6 Hz, H-7, sialic acid portion), 3.78(s, 3H, OCH$_3$), 2.43(dd, 1H, $J_{3e,3a}$=12.7 Hz, $J_{3e,4}$=4.6 Hz, H-3e, sialic acid portion), 2.14, 1.95, 1.92, 1.80(4s, 12H, 4AcO), 1.53, 1.50(2s, 6H, 2AcN), 1.09(d, 3H, $J_{5,6}$=6.4 Hz, H-6, fucose portion), 1.01(m, 2H, Me$_3$SiCH$_2$CH$_2$O).

$^{19}$F-NMR (CDCl$_3$; CFCl$_3$): δ −231(dt, JF,6H=46 Hz, JF,5H=21 Hz, 6-F, β-glucosamine portion).

Mass spectrometry: m/z for $C_{140}{}^{13}C_1H_{160}N_2O_{39}Fsi$ Calculated: 2553.0385 (M+H); Found: 2553.0472

EXAMPLE 14

Synthesis of 2-(Trimethylsilyl)ethyl O-(methyl 5-acetamide-4,7,8,9-tetra-O-acetyl-3,5-dideoxy-D-glycero-α-D-galacto-2-nonulopyranosylonate)-(2→3)-O-(2,4,6-tri-O-benzoyl-β-D-galactopyranosyl-(1→4)-O-[(2,3,4-tri-O-acetyl-α-L-fucopyranosyl)-(1→3)]-O-(2-acetamide-2,6-dideoxy-6-fluoro-β-D-glucopyranosyl-(1→3)-O-(2,4,6-tri-O-acetyl-β-D-galactopyranosyl)-(1→4)-2,3,6-tri-O-acetyl-β-D-glucopyranoside (Hereinafter Referred to as Compound (18))

39 mg (0.015 mmol) of compound (17) was dissolved in 6.8 ml of ethanol and 2.2 ml of acetic acid and subjected to catalytic reduction in the presence of 45 mg of 10% palladium-carbon under normal hydrogen pressure at 45° C. for 4 days. After filtering off the catalyst, the solvent was concentrated under reduced pressure. To the reside were added 5 ml of pyridine and 3 ml of acetic anhydride, followed by stirring at room temperature for 20 hours. After concentration under reduced pressure, the residue was purified by flash chromatography (eluent; n-hexane:ethyl acetate=1:6) and further purified by silica gel column chromatography (eluent: chloroform→1% methanol-chloroform→2% methanol-chloroform (concentration gradient)) to give compound (18) (22 mg, 68.3%). $C_{96}H_{123}N_2O_{48}FSi$ (2120.1) $[α]_D^{23}$=−24.2° (c=1.00, chloroform)

IR(KBr) νmax cm$^{-1}$: 3400(NH), 1740, 1230(ester), 1700, 1530(amide), 1070(ether), 860, 840 (Me$_3$Si), 720(Ph).

$^1$H-NMR (CDCl$_3$; TMS): δ 8.3–7.4(m, 15H, 3Ph), 5.75 (m, 1H, H-8, sialic acid portion), 5.27(dd, 1H, $J_{6,7}$=2.9 Hz, $J_{7,8}$=9.9 Hz, H-7, sialic acid portion), 5.35(d, 1H, $J_{1,2}$=3.3 Hz, H-1, fucose portion), 5.15(dd, 1H, $J_{2,3}$=$J_{3,4}$=9.3 Hz, H-3, glucose portion), 4.46(d, 1H, $J_{1,2}$=7.9 Hz, H-1, glucose portion), 3.83(s, 3H, OCH$_3$), 3.45(dd, 1H, J$_{2,3}$=10.0 Hz, J$_{3,4}$=3.5 Hz, H-3, galactose portion), 2.41(dd, 1H, J$_{3a,3e}$=12.7 Hz, J$_{3e,4}$=4.7 Hz, H-3e, sialic acid portion), 2.17, 2.12, 2.10, 2.09, 2.08, 2.08, 2.03, 2.02, 2.00, 2.00, 1.96, 1.92, 1.84(13s, 39H, 13AcO), 1.78, 1.56(2s, 6H, 2AcN), 1.11(d, 3H, J$_{5,6}$=6.5 Hz, H-6, fucose portion) 0.90(m, 2H, Me$_3$SiCH$_2$CH$_2$O).

$^{19}$F-NMR (CDCl$_3$; CFCl$_3$): δ −231(dt, JF,6H=47 Hz, JF,5H=20 Hz, 6-F, b-glucosamine portion).

Mass spectrometry: m/z for C$_{95}$$^{13}$C$_1$H$_{124}$N$_2$O$_{48}$Fsi Calculated: 2120.7110 (M+H); Found: 2120.7145

EXAMPLE 15

Synthesis of O-(Methyl 5-acetamide-4,7,8,9-tetra-O-acetyl-3,5-dideoxy-D-glycero-α-D-galacto-2-nonulopyranosylonate)-(2→3)-O-(2,4,6-tri-O-benzoyl-β-D-galactopyranosyl)-(1→4)-O-[(2,3,4-tri-O-acetyl-α-L-fucopyranosyl)-(1→3)]-O-(2-acetamide-2,6-dideoxy-6-fluoro-β-D-glucopyranosyl)-(1→3)-O-(2,4,6-tri-O-acetyl-β-D-galactopyranosyl)-(1→4)-2,3,6-tri-O-acetyl-D-glucopyranose (Hereinafter Referred to as Compound (19))

30 mg (0.014 mmol) of compound (18) was dissolved in 0.8 ml of anhydrous dichloromethane under argon atmosphere. The solution was cooled to 0° C. and 1.6 ml of trifluoroacetic acid was added dropwise. The mixture was stirred at the same temperature for 5 hours and then 2 ml of ethyl acetate was added. The mixture was concentrated at the same temperature under reduced pressure and then in vacuo. The residue was purified by silica gel column chromatography (eluent: dichloromethane→dichloromethane-methanol=30:1→20:1) to give compound (19) (24.5 mg, 85.7%). C$_{91}$H$_{111}$N$_2$O$_{48}$F (2019.8) [α]$_D^{25}$=−9.4° (c=0.75, chloroform)

IR(KBr) vmax cm$^{-1}$: 3600–3200(OH, NH), 1740, 1230 (ester), 1670, 1540(amide), 1070(ether) 720(Ph).

Mass spectrometry: m/z for C$_{91}$H$_{111}$N$_2$O$_{48}$F Calculated: 2020.6402 (M+H); Found: 2020.6386

EXAMPLE 16

Synthesis of O-(Methyl 5-acetamide-4,7,8,9-tetra-O-acetyl-3,5-dideoxy-D-glycero-α-D-galacto-2-nonulopyranosylonate)-(2→3)-O-(2,4,6-tri-O-benzoyl-β-D-galactopyranosyl)-(1→4)-O-[(2,3,4-tri-O-acetyl-α-L-fucopyranosyl)-(1→3)]-O-(2-acetamide-2,6-dideoxy-6-fluoro-β-D-galactopyranosyl)-(1→3)-O-(2,4,6-tri-O-acetyl-β-D-galactopyranosyl)-(1→4)-2,3,6-tri-O-acetyl-α-D-glucopyranosyl trichloroacetoimidate (Hereinafter Referred to as Compound (20))

49.0 mg (0.0242 mmol) of compound (19) was dissolved in 4 ml of anhydrous dichloromethane under argon atmosphere. The solution was cooled to 0° C. and 0.1 ml (0.997 mol) of trichloroacetonile and then 3 ml (0.02 mmol) of 1,8-diazabicyclo[5.4.0]undec-7-ene (DBU) were added, followed by stirring at the same temperature for 3 hours. After concentration under reduced pressure, the residue was purified by silica gel column chromatography (eluent: dichloromethane→dichloromethane-methanol=40:1→20:1) to give compound (20) (52.5 mg, 100%). C$_{93}$H$_{111}$N$_{348}$Cl$_3$F (2164.2) [α]$_D^{23}$=−0.90° (c=0.71, chloroform)

IR(KBr) vmax cm$^{-1}$: 3400(NH=C), 1740, 1230(ester), 1680, 1540(amide), 1070(ether), 760, 720(Ph).

$^1$H-NMR (CDCl$_3$; TMS): δ 8.65(s, 1H, NH=C), 8.2–7.4 (m, 15H, 3Ph), 6.47(d, 1H, J$_{1,2}$=3.7 Hz, H-1, glucose portion), 5.66(m, 1H, H-8, sialic acid portion) 5.36(d, 1H, J$_{1,2}$=3.8 Hz, H-1, fucose portion), 5.28(dd, 1H, J$_{6,7}$=2.7 Hz, J$_{7,8}$=9.9 Hz, H-7, sialic acid portion), 3.81(s, 3H, OCH$_3$), 3.48(dd, 1H, J$_{2,3}$=9.9 Hz, J$_{3,4}$=4.0 Hz, H-3, galactose portion), 2.41(dd, 1H, J$_{3a,3e}$=12.7 Hz, J$_{3a,4}$=4.4 Hz, H-3e, sialic acid portion), 2.17, 2.12, 2.10, 2.08, 2.08, 2.07, 2.04, 2.03, 2.00, 1.99, 1.96, 1.92, 1.84(13s, 39H, 13AcO), 1.78, 1.56(2s, 6H, 2AcN), 1.10(d, 3H, J$_{5,6}$=6.5 Hz, H-6, fucose portion), 0.90(m, 2H, Me$_3$SiCH$_2$CH$_2$O).

$^{19}$F-NMR (CDCl$_3$; CFCl$_3$): δ −231(dt, JF,6H=47 Hz, JF,5H=20 Hz, 6-F, β-glucosamine portion).

Mass spectrometry: m/z for C$_{93}$H$_{111}$N$_3$O$_{48}$Cl$_3$F Calculated: 2163.5498 (M+H); Found: 2163.5460

EXAMPLE 17

Synthesis of O-(Methyl 5-acetamide-4,7,8,9-tetra-O-acetyl-3,5-dideoxy-D-glycero-α-D-galacto-2-nonulopyranosylonate)-(2→3)-O-(2,4,6-tri-O-benzoyl-β-D-galactopyranosyl)-(1→4)-O-[(2,3,4-tri-O-acetyl-α-L-fucopyranosyl)-(1→3)]-O-(2-acetamide)-2,6-dideoxy-6-fluoro-β-D-glucopyranosyl)-( 1→3)-O-(2,4,6-tri-O-acetyl-β-D-galactopyranosyl)-(1→4)-2,3,6-tri-O-acetyl-β-D-glucopyranosyl)-(1→1)-(2S, 3R, 4E)-2-azide-3-O-benzoyl-4-octadecene-1,3-diol (Hereinafter Referred to as Compound (22))

45 mg (0.021 mmol) of compound (20) and 20 mg (0.047 mmol) of (2S, 3R, 4E)-2-azide-3-O-benzoyl-4-octadecene-1,3-diol (compound (21)) were dissolved in 1.5 ml of anhydrous dichloromethane under argon atmosphere. After addition of 0.45 g of activated Molecular Sieve (4 Å), the mixture was stirred at room temperature for 30 minutes and then cooled to 0° C. Subsequently 12 ml (0.10 mmol) of boron trifluoride-ether complex was added and the mixture was stirred at the same temperature for 3 hours. After dilution with dichloromethane, insoluble materials were filtered out and washed with dichloromethane. The filtrate and washing liquids were combined and washed with 1M aqueous sodium hydrogencarbonate solution and then with saturated sodium chloride aqueous solution, and dried over sodium sulfate. After concentration under reduced pressure, the residue was purified by silica gel column chromatography (eluent: dichloromethane→dichloromethane-methanol=50:1→30:1) to give compound (22) (36 mg, 71.5%). C$_{116}$H$_{148}$N$_5$O$_{50}$F (2431.5) [α]$_D^{23}$=−24.8° (c=1.13, chloroform)

IR(KBr) vmax cm$^{-1}$: 2950, 2850(methyl, methylene), 2100(azide), 1750, 1230(ester), 1680, 1550(amide), 1070 (ether), 800, 720(Ph).

$^1$H-NMR (CDCl$_3$; TMS): δ 8.2–7.4(m, 15H, 3Ph), 5.91 (dt, 1H, J$_{4,5}$=15.2 Hz, J$_{5,6}$=6.6 Hz, H-5, sphingosine portion), 5.67(m, 1H, H-8, sialic acid portion), 5.35(d, 1H, J$_{1,2}$=3.1 Hz, H-1, fucose portion), 5.27(dd, 1H, J$_{6,7}$=2.7 Hz, J$_{7,8}$=9.9 Hz, H-7, sialic acid portion), 5.14(dd, 1H, J$_{2,3}$=J$_{3,4}$=9.2 Hz, H-3, glucose portion), 4.49(d, 1H, J$_{1,2}$=7.7 Hz, H-1, glucose portion), 3.80(s, 3H, OCH$_3$), 3.44(dd, 1H, J$_{2,3}$=10.3 Hz, J$_{3,4}$=3.6 Hz, H-3, galactose portion), 2.40(dd, 1H, J$_{3a,3e}$=12.5 Hz, J$_{3e,4}$=4.4 Hz, H-3e, sialic acid portion), 2.18, 2.12, 2.10, 2.08, 2.08, 2.07, 2.04, 2.03, 2.00, 1.99, 1.96, 1.92, 1.84(13s, 39H, 13AcO), 1.79, 1.56(2s, 6H, 2AcN), 1.27(s, 22H, 11CH$_2$), 1.10(d, 3H, J$_{5,6}$=6.5 Hz, H-6, fucose portion), 0.87(t, 3H, J=6.6 Hz, CH$_3$CH$_2$).

$^{19}$F-NMR (CDCl$_3$; CFCl$_3$): δ −231(dt, JF,6H=47 Hz, JF,5H=20 Hz, 6-F, β-glucosamine portion).

Mass spectrometry: m/z for C$_{116}$H$_{148}$N$_5$O$_{50}$F Calculated: 2431.9288(M+H); Found: 2431.9262

EXAMPLE 18

Synthesis of O-(Methyl 5-acetamide-4,7,8,9-tetra-O-acetyl-3,5-dideoxy-D-glycero-α-D-galacto-2-nonulopyranosylonate)-(2→3)-O-(2,4,6-tri-O-benzoyl-β-D-galactopyranosyl)-(1→4)-O-[(2,3,4-tri-O-acetyl-α-L-fucopyranosyl)-(1→3)]-O-(2-acetamide-2,6-dideoxy-6- fluoro-β-D-glucopyranosyl)-(1→3)-O-(2,4,6-tri-O-acetyl-β-D-galactopyranosyl)-(1→4)-2,3,6-tri-O-acetyl-β-D-glucopyranosyl-(1→1)(2S, 3R, 4E)-3-O-benzoyl-2-octadecaneamide-4-octadecene-1,3-diol (Hereinafter Referred to as Compound (23))

43 mg (0.018 mmol) of compound (22) was dissolved in a mixed solvent of 4.17 ml of pyridine and 0.83 ml of water. The solution was cooled to 0° C. and hydrogen sulfide gas was passed through the solution for 60 hours. Then nitrogen gas was passed through the solution for 10 minutes to remove hydrogen sulfide remaining in the solution. The reaction mixture was concentrated and the residue was dissolved in 2 ml of anhydrous dichloromethane and cooled to 0° C. Thereto were added 13 mg (0.046 mmol) of octadecanoic acid and then 10 mg (0.050 mmol) of 1-ethyl-3-(3-dimethylaminopropyl)carbodiimide, followed by stirring at room temperature for 15 hours. The reaction mixture was diluted with dichloromethane, washed with water and dried over sodium sulfate. After concentration under reduced pressure, the residue was purified by silica gel column chromatography (eluent: dichloromethane→dichloromethane-methanol=50:1→30:1) to give compound (23) (32 mg, 68.0%). $C_{134}H_{184}N_3O_{51}F$ (2671.9) $[\alpha]_D^{24}$=−15.3° (c=0.83, chloroform)

IR(KBr) νmax cm$^{-1}$: 3400(NH), 2950, 2850(methyl, methylene), 1750, 1230(ester), 1680, 1530(amide), 1070 (ether), 810, 710(Ph).

$^1$H-NMR (CDCl$_3$; TMS): δ 8.2–7.4(m, 15H, 3Ph), 5.85 (dt,1H, $J_{4,5}$=14.1 Hz, $J_{5,6}$=6.9 Hz, H-5, sphingosine portion), 5.66(m, 1H, H-8, sialic acid portion), 5.35(d, 1H, $J_{1,2}$=2.8 Hz, H-1, fucose portion), 5.27(dd, 1H, $J_{6,7}$=2.8 Hz, $J_{7,8}$=9.8 Hz, H-7, sialic acid portion), 5.14(dd, 1H, $J_{2,3}$=$J_{3,4}$=9.3 Hz, H-3, glucose portion), 4.43(d, 1H, $J_{1,2}$=7.7 Hz, H-1, glucose portion), 3.80(s, 3H, OCH$_3$), 3.43(dd, 1H, $J_{2,3}$=10.0 Hz, $J_{3,4}$=3.6 Hz, H-3, glucosge portion), 2.41(dd, 1H, $J_{3a,3e}$=12.7 Hz, $J_{3e,4}$=4.7 Hz, H-3e, sialic acid portion), 2.18, 2.12, 2.10, 2.08, 2.08, 2.07, 2.04, 2.03, 2.00, 1.99, 1.96, 1.92, 1.84(13s, 39H, 13AcO), 1.78, 1.56(2s, 6H, 2AcN), 1.26(s, 52H, 26CH$_2$), 1.10(d, 3H, $J_{5,6}$=6.4 Hz, H-6, fucose portion), 0.87(t, 6H, J=6.6 Hz, 2CH$_3$CH$_2$).

$^{19}$F-NMR (CDCl$_3$; CFCl$_3$): δ −231(dt, JF,6H=48 Hz, JF,5H=21 Hz, 6-F, β-glucosamine portion).

Mass spectrometry: m/z for $C_{134}H_{185}N_3O_{51}F$ Calculated: 2671.1959 (M+H); Found: 2671.1943

EXAMPLE 19

Synthesis of O-(5-Acetamide-3,5-dideoxy-D-glycero-α-D-galacto-2-nonulopyranosylonic acid)-(2→3)-O-β-D-glucopyranosyl-(1→4)-O-[α-L-fucopyranosyl-(1→3)]-O-(2-acetamide-2,6-dideoxy-6-fluoro-β-D-galactopyranosyl)-(1→3)-O-β-D-galactopyranosyl)-(1→4)-β-D-glucopyranosyl-(1→1)(2S, 3R, 4E)-2-octadecaneamide-4-octadecene-1,3-diol (Hereinafter Referred to as Compound (24))

32.0 mg (0.0119 mmol) of compound (23) was dissolved in 2 ml of absolute methanol. Subsequently 10 mg (0.19 mmol) of sodium methoxide was added under argon atmosphere at room temperature and the mixture was stirred at 40° C. for 24 hours. The mixture was allowed to cool to room temperature and then 0.18 ml of water was added, followed by stirring for 8 hours. The reaction mixture was neutralized with a column of Amberlite IR120B(H$^+$)(eluent: methanol). After concentration under reduced pressure, the residue was purified by gel filtration column chromatography on Sephadex LH20 (15 g) (eluent; chloroform:methanol:water=50:40:7) to give compound (24) (18.5 mg, 91.7%). $C_{79}H_{140}N_3O_{34}F$(1695.0) $[\alpha]_D^{24}$=−16.5° (c=0.40, chloroform:methanol:water=50:40:7)

IR(KBr) νmax cm$^{-1}$: 3700–3200(OH, NH), 2920, 2850 (methyl, methylene), 1700(carboxylic acid), 1650, 1540 (amide), 1070(ether).

$^1$H-NMR ((CD$_3$)$_2$SO-D$_2$O=50:1; TMS): δ 5.32(dt, 1H, $J_{4,5}$=15.3 Hz, $J_{5,6}$=6.6 Hz, H-5, sphingosine portion), 5.34 (dd, 1H, $J_{3,4}$=7.3 Hz, $J_{4,5}$=15.3 Hz, H-4, sphingosine portion), 5.10(d, 1H, $J_{1,2}$=3.5 Hz, H-1, fucose portion), 4.74(d, 1H, $J_{1,2}$=6.8 Hz, H-1, N-acetylglucosamine portion), 4.16(d, 1H, $J_{1,2}$=7.8 Hz, glucose portion), 2.77(dd, 1H, $J_{3a,3e}$=12.2 Hz, $J_{3e,4}$=4.8 Hz, H-3e, sialic acid portion), 1.89, 1.78(2s, 6H, 2AcN), 1.23(s, 52H, 26CH$_2$), 0.96(d, 3H, $J_{5,6}$=6.3 Hz, H-6, fucose portion), 0.85(t, 6H, J=6.4 Hz, 2CH$_3$CH$_2$).

$^{19}$F-NMR [(CD$_3$)$_2$SO-D$_2$O=50:1; CFCL$_3$]: δ −230(dt, JF,6H=46 Hz, JF,5H=20 Hz, 6-F, β-glucosamine portion). Elemental analysis: $C_{79}H_{140}N_3O_{34}F$.2.5H$_2$O.1.75CHCl$_3$ Calculated: C; 49.77, H; 7.59, N; 2.16; Found: C; 49.59, H; 7.69, N; 2.15.

EXAMPLE 20

Synthesis of 2-(Trimethylsilyl)ethyl O-(5-acetamide-3,5-dideoxy-D-glycero-α-D-galacto-2-nonulopyranosylonic acid)-(2→3)-O-β-D-galactopyranosyl-(1→4)-O-[60-L-fucopyranosyl-( 1→3)]-O-(2-acetamide-2,6-dideoxy-6-fluoro-β-D-galactopyranosyl)-(1→3)-O-β-D-galactopyranosyl)-(1→4)-β-D-glucopyranoside (Hereinafter Referred to as Compound (25)) 19.0 mg (0.0089 mmol) of compound (18) was dissolved in 1.5 ml of absolute methanol under argon atmosphere. After addition of 35 mg (0.65 mmol) of sodium methoxide at room temperature, the mixture was stirred at 40° C. for 24 hours. The mixture was allowed to cool to room temperature and then 0.9 ml of water was added, followed by stirring for 7.5 hours. The reaction mixture was neutralized with a column of Amberlite IR120B(H$^+$)(eluent: methanol). After concentration under reduced pressure, the residue was purified by gel filtration column chromatography on Sephadex LH20 (10 g) (eluent: methanol) to give compound (25) (5.0 mg, 44.7%). C48H$_{83}$N$_2$O$_{32}$FSi (1247.3) $[\alpha]_D^{\leq}$=−30.5° (c=0.22, methanol)

IR(KBr) νmax cm$^{-1}$: 3700–3200(OH, NH), 2930, 2860 (methyl, methylene), 1730(carboxylic acid), 1630, 1560 (amide), 1070(ether).

$^1$H-NMR [(CD$_3$)OD; TMS]: δ 5.10(d, 1H, $J_{1,2}$=3.5 Hz, H-1, fucose portion), 4.27(d, 1H, $J_{1,2}$=7.8 Hz, glucose portion), 2.80(dd, 1H, $J_{3a,3e}$=12.2 Hz, $J_{3e,4}$=4.8 Hz, H-3e, sialic acid portion), 1.97, 1.95(2s, 6H, 2AcN), 1.12(d, 3H, $J_{5,6}$=6.7 Hz, H-6, fucose portion), 1.00(m, 2H, CH$_2$SiMe$_3$).

$^{19}$F-NMR (CD$_3$OD; CFCl$_3$): δ −230(dt, JF,6H=48 Hz, JF,5H=29 Hz, 6-F, β-glucosamine portion).

Mass spectrometry: m/z for C$_{48}$H$_{84}$N$_2$O$_{32}$FSi Calculated: 1247.4761 (M+H); Found: 1247.4742

EXAMPLE 21

Synthesis of 2-(Tetradecyl)hexadecyl O-(2,3,4-tri-O-benzyl-α-L-fucopyranosyl-(1→3)-4-O-acetyl-2,6-dideoxy-6-fluoro-2-phthalimide-β-D-glucopyranoside (Hereinafter Referred to as Compound (27))

50 mg (0.063 mmol) of compound (11) and 50 mg (0.11 mmol) of 2-(tetradecyl)hexadecyl-1-ol compound (26) were dissolved in 2 ml of anhydrous dichloromethane. Under argon atmosphere, 0.2 g of Molecular Sieve (4 Å) was added and the mixture was stirred at room temperature for 11 hours. The reaction mixture was cooled to −20° C. and 56 mg (0.25 mmol) of N-iodosuccinimide and then 10 mg (0.02 mmol) of scandium trifluoromethanesulfonate were added, followed by stirring at −20 to −15° C. for 50 minutes. The mixture was diluted with dichloromethane and filtrated through a layer of Celite and then the Celite layer was washed with dichloromethane. The filtrate and washing liquids were combined, washed with 1M sodium hydrogencarbonate aqueous solution and then with saturated sodium chloride aqueous solution, and dried over sodium sulfate. After concentration under reduced pressure, the residue was purified by flash chromatography (eluent; n-hexane:ethyl acetate=4:1) to give compound (27) (41 mg, 51.2%). $C_{73}H_{104}NO_{11}F$ (1190.63) $[\alpha]_D^{24}$ +11.2° (c=0.93, chloroform)

IR(KBr) νmax cm$^{-1}$: 1750, 1230(ester), 1720(imide), 1080(ether), 800, 740(Ph).

$^1$H-NMR (CDCl$_3$; TMS): δ 7.9–6.8(m, 14H, Phthal+3Ph), 5.66(d, H, $J_{1,2}$=8.4 Hz, H-1, β-glucosamine portion), 2.02(s, 3H, COCH$_3$), 1.26(s, 52H, 26CH$_2$), 0.96(d, 3H, $J_{5,6}$=6.5 Hz, H-6, fucose portion), 0.84(t, 6H, J=6.4 Hz, 2CH$_3$CH$_2$).

$^{19}$F-NMR (CD$_3$OD; CFCl$_3$): δ –230(dt, JF,6H=47 Hz, JF,5H=19 Hz, 6-F, β-glucosamine portion).

Mass spectrometry: m/z for $C_{73}H_{105}NO_{11}F$ Calculated: 1190.767232 (M+H); Found: 1190.7653

EXAMPLE 22
Synthesis of 2-(Tetradecyl)hexadecyl O-(2,3,4-tri-O-benzyl-α-L-fucopyranosyl-(1→3)-2-acetamide-4-O-acetyl-2,6-dideoxy-6-fluoro-β-D-glucopyranoside (Hereinafter Referred to as Compound (28))

41 mg (0.034 mmol) of compound (27) was dissolved in 4.5 ml of n-butanol. After addition of 1.5 ml of ethylenediamine, the mixture was heated with stirring under argon atmosphere at 82° C. for 24 hours. The reaction mixture was concentrated under reduced pressure at temperatures not higher than 60° C. To the reside were added 8 ml of pyridine and then 4.5 ml of acetic anhydride, followed by stirring at room temperature for 16 hours. After re-concentration under reduced pressure, the residue was purified by flash chromatography (eluent; n-hexane:ethyl acetate=3:1) to give compound (28) (33 mg, 86.9%). $C_{67}H_{104}N_{10}F$ (1102.56)

IR(KBr) νmax cm$^{-1}$: 1750, 1230(ester), 1660, 1500 (amide), 1080(ether), 800, 740(Ph).

$^1$H-NMR (CDCl$_3$; TMS): δ 7.4–7.0(m, 15H, 3Ph), 5.36(d, H, $J_{1,2}$=8.4 Hz, H-1, β-glucosamine portion), 2.04(s, 3H, COCH$_3$), 1.37(s, 3H, NAc), 1.26(s, 52H, 26CH$_2$), 1.03(d, $J_{5,6}$=6.4 Hz, H-6, fucose portion), 0.84(t, 6H, J=6.4 Hz, 2CH$_3$CH$_2$).

$^{19}$F-NMR (CD$_3$OD; CFCl$_3$): δ –230(dt, JF,6H=48 Hz, JF,5H=19 Hz, 6-F, β-glucosamine portion).

Mass spectrometry: m/z for $C_{67}H_{105}O_{10}FN$ Calculated: 1102.7723 (M+H); Found: 1102.7698

EXAMPLE 23
Synthesis of 2-(Tetradecyl)hexadecyl O-(2,3,4-tri-O-benzyl-α-L-fucopyranosyl-(1→3)-2-acetamide-2,6-dideoxy-6-fluoro-β-D-glucopyranosyl (Hereinafter Referred to as Compound (29))

50 mg (0.045 mmol) of compound (28) was dissolved in 10 ml of absolute methanol, and 12 mg (0.22 mmol) of sodium methoxide was added under argon atmosphere at room temperature for 6.5 hours. The reaction mixture was neutralized with a column of Amberlite IR120B(H$^+$)(eluent: methanol). The eluate was concentrated under reduced pressure and the residue was purified by flash chromatography (eluent; n-hexane:ethyl acetate=3:1) to give compound (29) (40 mg, 83.3%). $C_{65}H_{102}NO_9F$ (1060.52)

IR(KBr) νmax cm$^{-1}$: 3700–3200(OH, NH),1660, 1500 (amide), 1080(ether), 800, 740(Ph).

$^1$H-NMR (CDCl$_3$; TMS): δ 7.4–7.0(m, 15H, 3Ph), 5.36(d, H, $J_{1,2}$=8.4 Hz, H-1, β-flucosamine portion), 1.40(s, 3H, NAc), 1.26(s, 52H, 26CH$_2$), 1.03(d, $J_{5,6}$=6.4 Hz, H-6, fucose portion), 0.84(t, 6H, J=6.4 Hz, 2CH$_3$CH$_2$).

$^{19}$F-NMR (CD$_3$OD; CFCl$_3$): δ –231(dt, JF,6H=47 Hz, JF,5H=18 Hz, 6-F, β-glucosamine portion).

Mass spectrometry: m/z for $C_{65}H_{102}NO_9FNa$ Calculated: 1082.7437 (M+Na); Found: 1082.7422

EXAMPLE 24
Synthesis of 2-(Tetradecyl)hexadecyl O-(methyl 5-acetamide-4,7,8,9-tetra-O-acetyl-3,5-dideoxy-D-glycero-α-D-galacto-2-nonulopyranosylonate)-(2→3)-O-(2,4,6-tri-O-benzoyl-β-D-galactopyranosyl-(1→4)-O-[(2,3,4-tri-O-benzyl-α-L-fucopyranosyl)-(1→3)]-2-acetamide-2,6-dideoxy-6-fluoro-β-D-glucopyranoside (Hereinafter Referred to as Compound (30))

60 mg (0.057 mmol) of compound (29) and 150 mg (0.151 mmol) of methyl O-(methyl 5-acetamide-4,7,8,9-tetra-O-acetyl-3,5-dideoxy-D-glycero-α-D-galacto-2-nonulopyranosylonate)-(2→3)-2,4,6-tri-O-benzoyl-1-thio-β-D-galactopyranoside (compound (16)) were dissolved in 2 ml of anhydrous dichloromethane under argon atmosphere. To the solution was added 140 mg of activated Molecular Sieve (4 Å). The reaction mixture was stirred at room temperature for 3.5 hours and then a mixture of 70 mg (0.27 mmol) of dimethyl(methylthio)sulfonium triflate (DMTST) and 70 mg of activated Molecular Sieve (4 Å) was added at room temperature. The reaction mixture was stirred at room temperature for 22 hours. After cooling with ice, 0.36 ml of methanol and 0.18 ml of triethylamine were added and the mixture was stirred at room temperature for 30 minutes. The reaction mixture was diluted with dichloromethane and then filtered and washed. The filtrate and washing liquids were combined, washed with water, dried over sodium sulfate and concentrated under reduced pressure. The residue was purified by flash chromatography (eluent; n-hexane:ethyl acetate=1:3) to give compound (30) (28 mg, 24.8%). $C_{112}H_{151}N_2O_{29}F$ (1994.42)

IR(KBr) νmax cm$^{-1}$: 3400(NH), 1740, 1270(ester), 1680, 1500(amide), 1070(ether), 740, 710(Ph).

$^1$H-NMR (CDCl$_3$; TMS): δ 8.3–7.0(m, 30H, 6Ph), 5.65 (m, 1H, H-8, sialic acid portion), 5.23(dd, 1H, $J_{7,8}$=12.4 Hz, $J_{6,7}$=2.6 Hz, H-7, sialic acid portion), 3.78(s, 3H, OCH$_3$), 2.43(dd, 1H, $J_{3e,3a}$=12.7 Hz, $J_{3e,4}$=4.6 Hz, H-3e, sialic acid portion), 2.14, 1.95, 1.92, 1.80(4s, 12H, 4AcO), 1.53, 1.50 (2s, 6H, 2AcN), 1.26(s, 52H, 26CH$_2$), 1.09(d, 3H, $J_{5,6}$=6.4 Hz, H-6, fucose portion), 0.84(t, 6H, J=6.4 Hz, 2CH$_3$CH$_2$).

$^{19}$F-NMR (CD$_3$OD; CFCl$_3$): δ –231(dt, JF,6H=46 Hz, JF,5H=21 Hz, 6-F, β-glucosamine portion).

Mass spectrometry: m/z for $C_{112}H_{152}N_2O_{29}F$ Calculated: 2008.0465 (M+H); Found: 2008.0425

EXAMPLE 25
Synthesis of 2-(Tetradecyl)hexadecyl O-(methyl 5-acetamide-4,7,8,9-tetra-O-acetyl-3,5-dideoxy-D-glycero-α-D-galacto-2-nonulopyranosylonate)-(2→3)-O-(2,4,6-tri-O-benzoyl-β-D-galactopyranosyl-(1→4)-O-[(2,3,4-tri-O-acetyl-α-L-fucopyranosyl)-(1→3)]-2-acetamide-2,6-dideoxy-6-fluoro-β-D-glucopyranoside (Hereinafter Referred to as Compound (31))

30 mg (0.015 mmol) of compound (30) was dissolved in 6.8 ml of ethanol and 2.2 ml of acetic acid and subjected to catalytic reduction in the presence of 45 mg of 10% palladium-carbon under normal hydrogen pressure at 45° C. for 4 days. After filtering off the catalyst, the solvent was concentrated under reduced pressure. To the reside were added 5 ml of pyridine and 3 ml of acetic anhydride, followed by stirring at room temperature for 20 hours. After concentration of the reaction mixture under reduced pressure, the residue was purified by silica gel column chromatography (eluent: chloroform→1% methanol-chloroform→2% methanol-chloroform (concentration gradient)) to give compound (31) (20 mg, 71.3%). $C_{97}H_{139}N_2O_{32}F$ (1864.16)

IR(KBr) vmax cm$^{-1}$: 3400(NH), 1740, 1230(ester), 1700, 1530(amide), 1070(ether), 740, 720(Ph).

$^1$H-NMR (CDCl$_3$; TMS): δ 8.3–7.4(m, 15H, 3Ph), 5.63 (m, 1H, H-8, sialic acid portion), 5.27(dd, 1H, $J_{6,7}$=2.9 Hz, $J_{7,8}$=9.9 Hz, H-7, sialic acid portion), 5.35(d, 1H, $J_{1,2}$=3.3 Hz, H-1, fucose portion), 3.77(s, 3H, OCH$_3$), 2.51(dd, 1H, $J_{3a,3e}$=12.7 Hz, $J_{3e,4}$=4.7 Hz, H-3e, sialic acid portion), 2.2–1.84(7s, 21H, 7AcO), 1.70, 1.43(2s, 6H, 2AcN), 1.26(s, 52H, 26CH$_2$), 1.33(d, 3H, $J_{5,6}$=6.5 Hz, H-6, fucose portion), 0.84(t, 6H, J=6.4 Hz, 2CH$_3$CH$_2$).

$^{19}$F-NMR (CD$_3$OD; CFCl$_3$): δ −231(dt, JF,6H=47 Hz, JF,5H=20 Hz, 6-F, β-glucosamine portion).

Mass spectrometry: m/z for $C_{97}H_{140}N_2O_{32}F$ Calculated: 1863.9373 (M+H); Found: 1863.9345

EXAMPLE 26

Synthesis of 2-(Tetradecyl)hexadecyl O-(5-acetamide-3,5-dideoxy-D-glycero-α-D-galacto-2-nonulopyranosylonic acid)-(2→3)-O-β-D-galactopyranosyl-(1→4)-O-[α-L-fucopyranosyl-(1→3)]-2-acetamide-2,6-dideoxy-6-fluoro-β-D-glucopyranoside (Hereinafter Referred to as Compound (32))

19 mg (0.010 mmol) of compound (31) was dissolved in 1.5 ml of absolute methanol, and 35 mg (0.65 mmol) of sodium methoxide was added under argon atmosphere at room temperature. The reaction mixture was stirred at 40° C. for 24 hours. The mixture was allowed to cool to room temperature and then 0.9 ml of water was added, followed by stirring for 7.5 hours. The reaction mixture was neutralized with a column of Amberlite IR120B(H$^+$)(eluent: methanol) and the eluate was concentrated under reduced pressure. The residue was purified by gel filtration column chromatography on Sephadex LH20 (10 g) (eluent; chloroform:methanol=1:1) to give compound (32) (6.0 mg, 47.5%). C61H$_{105}$N$_2$O$_{22}$F (1237.50) $[\alpha]_D^{24}$−17.1° (c=0.40, chloroform:methanol=1:1)

IR(KBr) vmax cm$^{-1}$: 3700–3200(OH, NH), 2930, 2860 (methyl, methylene), 1730(carboxylic acid), 1630, 1560 (amide), 1070(ether).

$^1$H-NMR [DMSO-d$_6$; TMS]: δ 5.16(d, 1H, $J_{1,2}$=3.8 Hz, H-1, fucose portion), 2.85(dd, 1H, $J_{3a,3e}$=12.2 Hz, $J_{3e,4}$=4.8 Hz, H-3e, sialic acid portion), 1.97, 1.87(2s, 6H, 2AcN), 1.26(s, 52H, 26CH$_2$), 0.91(d, 3H, $J_{5,6}$=6.4 Hz, H-6, fucose portion), 0.87(t, 6H, 2CH$_3$CH$_2$).

$^{19}$F-NMR (CD$_3$OD; CFCl$_3$): δ −230(dt, JF,6H=48 Hz, JF,5H=29 Hz, 6-F, 8-glucosamine portion).

Mass spectrometry: m/z for $C_{61}H_{105}N_2O_{22}FNa$ Calculated: 1259.7041 (M+Na); Found: 1259.7010

Elemental analysis: $C_{61}H_{105}N_2O_{22}F\cdot2.5H_2O\cdot2.0CHCl_3$ Calculated: C; 49.74, H; 7.42, N; 1.84; Found: C; 49.54, H; 7.60, N; 1.90.

EXAMPLE 27

Synthesis of 2-(Tetradecyl)hexadecyl O-(2,4,6-tri-O-benzoyl-3-O-levulinyl-β-D-galactopyranosyl)-(1→4)-O-[(2,3,4-tri-O-benzyl-α-L-fucopyranosyl)-(1→3)]-2-acetamide-2,6-dideoxy-6-fluoro-β-D-glucopyranoside (Hereinafter Referred to as Compound (34))

60 mg (0.057 mmol) of compound (29) and 65 mg (0.088 mmol) of 2,4,6-tri-O-benzoyl-3-O-levulinyl-α-D-galactopyranosyl trichloroacetoimidate (compound (33)) were dissolved in 2 ml of anhydrous dichloromethane. Added to the solution under argon atmosphere was 100 mg of Molecular Sieve (4 Å), and the reaction mixture was stirred at room temperature for 16 hours.

The mixture was cooled with ice and 1 μl of boron trifluoride-ether complex was added at 4° C. The mixture was stirred at room temperature for 3 hours and then 20 μl of triethylamine was added. Immediately after dilution with dichloromethane, the mixture was filtrated through a layer of Celite, followed by washing with dichloromethane. A mixture of the filtrate and washing liquids was washed with 1M sodium hydrogencarbonate aqueous solution and then with saturated sodium chloride aqueous solution and dried over sodium sulfate. After concentration under reduced pressure, the residue was purified by silica gel column chromatography (eluent: dichloromethane→dichloromethane-methoanol=100:1→50:1→30:1) to give compound (32) (66 mg, 71.5%). $C_{97}H_{130}NO_{19}F$ (1633.09)

$^1$H-NMR (CDCl$_3$; TMS): δ 8.3–7.0(m, 30H, 6Ph), 4.96(d, 1H, $J_{1,2}$=9.9 Hz, H-1, galactose portion), 2.35–2.80(m, 4H, MeCOCH$_2$CH$_2$), 1.50(s, 3H, AcN), 1.26(s, 52H, 26CH$_2$), 1.09(d, 3H, $J_{5,6}$=6.4 Hz, H-6, fucose portion), 0.84(t, 6H, J=6.4 Hz, 2CH$_3$CH$_2$).

$^{19}$F-NMR (CD$_3$OD; CFCl$_3$): δ −231(dt, JF,6H=46 Hz, JF,5H=21 Hz, 6-F, β-glucosamine portion).

Mass spectrometry: m/z for $C_{97}H_{131}NO_{19}F$ Calculated: 1662.9299 (M+H); Found: 1662.9277

EXAMPLE 28

Synthesis of 2-(Tetradecyl)hexadecyl O-(2,4,6-tri-O-benzoyl-3-O-levulinyl-β-D-galactopyranosyl)-(1→4)-O-[(2,3,4-tri-O-acetyl-α-L-fucopyranosyl)-(1→3)]-2-acetamide-2,6-dideoxy-6-fluoro-β-D-glucopyranoside (Hereinafter Referred to as Compound (35))

65 mg (0.040 mmol) of compound (34) was dissolved in 6.8 ml of ethanol and 2.2 ml of acetic acid and subjected to catalytic reduction in the presence of 75 mg of 10% palladium-carbon under normal hydrogen pressure at 45° C. for 24 hours. After filtering off the catalyst, the solvent was concentrated under reduced pressure. To the reside were added 15 ml of pyridine and 9 ml of acetic anhydride, followed by stirring at room temperature for 20 hours. After concentration under reduced pressure, the residue was purified by silica gel column chromatography (eluent: chloroform→1% methanol-chloroform→2% methanol-chloroform (concentration gradient)) to give compound (35) (41 mg, 69.2%). $C_{82}H_{118}NO_{22}F$ (1488.83)

$^1$H-NMR (CDCl$_3$; TMS): δ 8.3–7.4(m, 15H, 3Ph), 5.35(d, 1H, $J_{1,2}$=3.3 Hz, H-1, fucose portion), 4.73(d, 1H, $J_{1,2}$=8.6 Hz, H-1, galactose portion), 2.35–2.8(m, 4H, MeCOCH$_2$CH$_2$), 2.2–1.8(3s, 9H, 3AcO), 1.52(s, 3H, AcN), 1.26(52H, 26CH$_2$), 1.11(d, 3H, $J_{5,6}$=6.5 Hz, H-6, fucose portion), 0.84(t, 6H, J=6.4 Hz, 2CH$_3$CH$_2$).

$^{19}$F-NMR (CD$_3$OD; CFCl$_3$): δ −231(dt, JF,6H=47 Hz, JF,5H=20 Hz, 6-F, β-glucosamine portion).

Mass spectrometry: m/z for $C_{82}H_{119}NO_{22}F$ Calculated: 1488.8208 (M+H); Found: 1488.8179

EXAMPLE 29

Synthesis of 2-(Tetradecyl)hexadecyl O-(2,4,6-tri-O-benzoyl-β-D-galactopyranosyl-(1→4)-O-[(2,3,4-tri-O-acetyl-α-L-fucopyranosyl)-(1→3)]-2-acetamide-2,6-dideoxy-6-fluoro-β-D-glucopyranoside (Hereinafter Referred to as Compound (36))

41 mg (0.028 mmol) of compound (35) was dissolved in 1 ml of ethanol. Added to the solution under argon atmosphere was 2.6 mg (0.030 mmol) of hydrazine acetate, and the mixture was stirred at room temperature for 3 hours. The mixture was concentrated under reduced pressure and the residue was purified by silica gel column chromatography (eluent: chloroform→1% methanol-chloroform→2% methanol-chloroform (concentration gradient)) to give compound (36) (25 mg, 65.4%). $C_{77}H_{112}NO_{20}F$ (1390.73)

IR(KBr) νmax $cm^{-1}$: 3700–3200(OH, NH), 1660, 1500 (amide), 1070(ether), 740, 700(Ph).

$^{1}$H-NMR (CDCl$_3$; TMS): δ 8.3–7.4(m, 15H, 3Ph), 5.60(d, 1H, $J_{1,2}$=3.1 Hz, H-1, fucose portion), 4.68(d, 1H, $J_{1,2}$=8.6 Hz, H-1, galactose portion), 2.2–1.8(3s, 9H, 3AcO), 1.52(s, 3H, AcN), 1.26(52H, 26CH$_2$), 1.18(d, 3H, $J_{5,6}$=6.5 Hz, H-6, fucose portion), 0.84(t, 6H, J=6.4 Hz, 2CH$_3$CH$_2$).

$^{19}$F-NMR (CD$_3$OD; CFCl$_3$): δ −231(dt, JF,6H=47 Hz, JF,5H=20 Hz, 6-F, β-flucosamine portion).

Mass spectrometry: m/z for $C_{77}H_{112}NO_{20}FNa$ Calculated: 1412.7660 (M+Na); Found: 1412.7638

EXAMPLE 30
Synthesis of 2-(Tetradecyl)hexadecyl O-(2,4,6-tri-O-benzoyl-3-O-sulfo-β-D-galactopyranosyl-(1→4)-O-[(2,3,4-tri-O-acetyl-α-L-fucopyranosyl)-(1→3)]-2-acetamide-2,6-dideoxy-6-fluoro-β-D-glucopyranoside pyridine salt (Hereinafter Referred to as Compound (37))

25 mg (0.018 mmol) of compound (36) was dissolved in 0.5 ml of anhydrous N,N-dimethylformamide under argon atmosphere. To the solution was added 15 mg (0.094 mmol) of sulfur trioxide-pyridine complex salt, and the mixture was stirred at room temperature for 1 hour. After addition of 0.1 ml of methanol, the mixture was further stirred for 30 minutes. The mixture was concentrated under reduced pressure and then in vacuo. The residue was purified by silica gel column chromatography (eluent: chloroform→2% methanol-chloroform→5% methanol-chloroform→10% methanol-chloroform (concentration gradient)) to give compound (37) (26 mg, 93.3%). $C82H_{117}N_{23}O_{23}FS$ (1549.88)

$^{1}$H-NMR (CDCl$_3$; TMS): δ 8.3–7.1(m, 20H, 3Ph, pyridine), 2.2–1.8(3s, 9H, 3AcO), 1.52(s, 3H, AcN), 1.26 (52H, 26CH$_2$), 1.05(d, 3H, $J_{5,6}$=6.4 Hz, H-6, fucose portion), 0.84(t, 6H, J=6.4 Hz, 2CH$_3$CH$_2$).

$^{19}$F-NMR (CD$_3$OD; CFCl$_3$): δ −230(dt, JF,6H=48 Hz, JF,5H=20 Hz, 6-F, β-glucosamine portion).

EXAMPLE 31
Synthesis of 2-(Tetradecyl)hexadecyl O-(3-O-sulfo-β-D-galactopyranosyl-(1→4)-O-[α-L-fucopyranosyl-(1→3)]-2-acetamide-2,6-dideoxy-6-fluoro-β-D-glucopyranoside.sodium salt (Hereinafter Referred to as Compound (38))

26 mg (0.017 mmol) of compound (37) was dissolved in a mixture of 1 ml of absolute methanol and 0.5 ml of anhydrous tetrahydrofuran under argon atmosphere and 2 mg (0.037 mmol) of sodium methoxide was added. The mixture was stirred at room temperature for 24 hours. The reaction mixture was concentrated under reduced pressure and the residue was purified by gel filtration column chromatography on Sephadex LH20 (15 g) (eluent; chloroform:methanol:water=50:40:7) to give compound (38) (16 mg, 90.5%). $C_{50}H_{93}NO_{17}FSNa$ (1054.34) $[α]_D^{23}$=−20.5° (c=0.80, methanol:chloroform=1:1)

$^{1}$NMR (C$_5$D$_5$N; TMS): δ 5.10(d, 1H, $J_{1,2}$=3.5 Hz, H-1, fucose portion), 1.91(s, 3H, AcN), 1.26(52H, 26CH$_2$), 1.05 (d, 3H, $J_{5,6}$=6.4 Hz, H-6, fucose portion), 0.84(t, 6H, J=6.4 Hz, 2CH$_3$CH$_2$).

$^{19}$F-NMR (C$_5$D$_5$N; CFCl$_3$): δ −230(dt, JF,6H=48 Hz, JF,5H=28 Hz, 6-F, β-glucosamine portion).

Mass spectrometry: m/z for $C_{50}H_{93}NO_{17}FS$ Calculated: 1030.6 (M+Na)—; Found: 1030.5

EXAMPLE 32
Synthesis of O-(2,3,4-Tri-O-benzyl-α-L-fucopyranosyl)-(1→3)-4-O-acetyl-2,6-dideoxy-6-fluoro-2-phthalimide-D-glucopyranosyl chloride (Hereinafter Referred to as Compound (39))

180 mg (0.234 mmol) of compound (9) in a vessel equipped with a calcium chloride tube was cooled with ice and dissolved in 2 ml of acetyl chloride. The solution was stirred at room temperature for 16 hours. The reaction mixture was diluted with chloroform and washed with iced water, saturated sodium hydrogencarbonate aqueous solution and saturated sodium chloride aqueous solution and dried over magnesium sulfate. The mixture was concentrated under reduced pressure and the residue was dried in vacuo to give crude compound (39) (0.18 g, 97.7%). $C_{43}H_{43}N_{10}FCl$ (788.27)

Mass spectrometry: m/z for $C_{43}H_{44}NO_{10}FCl$ Calculated: 788.2638 (M+H); Found: 788.2651

EXAMPLE 33
Synthesis of O-(2,3,4-Tri-O-benzyl-α-L-fucopyranosyl)-(1→3)-4-O-acetyl-1,5-anhydro-2,6-dideoxy-6-fluoro-2-phthalimide-D-glucitol (Hereinafter Referred to as Compound (40))

180 mg (0.228 mmol) of compound (39) was dissolved in 2 ml of anhydrous toluene under argon atmosphere. While the solution was stirred, 19 mg (0.12 mmol) of 2,2'-azobisisobutylonitrile and then 80 μl (0.30 mmol) of tributyltin hydride were added. The reaction mixture was stirred with heating at 90° C. for 45 minutes. The mixture was allowed to cool and then a mixture of 50 mg of potassium fluoride dihydrate and 0.2 ml of water was added and the resultant mixture was vigorously stirred at room temperature for 15 minutes. The reaction mixture was filtrated through a layer of Celite, and the Celite layer was washed with chloroform. A mixture of the filtrate and washing liquids was washed with water, dried over sodium sulfate and concentrated under reduced pressure. The residue was purified by flash chromatography (eluent; n-hexane:ethyl acetate=3:1) to give compound (40) (160 mg, 93.0%). $C_{43}H_{44}N_{10}F$ (753.82)

$^{1}$H-NMR (CDCl$_3$; TMS): δ 7.9–6.9(m, 19H, Phthal+3Ph), 4.57(d, 1H, $J_{1,2}$=3.2 Hz, H-1, fucose portion), 3.07(dd, 1H, Jgem=J$_{lax,2}$=8.1 Hz, H-1ax, glucosamine portion), 2.00(s, 3H, COCH$_3$), 0.96(d, 3H, $J_{5,6}$=6.5 Hz, H-6, fucose portion).

$^{19}$F-NMR (CD$_3$OD; CFCl$_3$): δ −232(dt, JF,6H=47 Hz, JF,5H=20 Hz, 6-F, glucitol portion).

Mass spectrometry: m/z for $C_{43}H_{45}NO_{10}F$ Calculated: 754.3028 (M+H); Found: 754.3020

EXAMPLE 34
Synthesis of O-(2,3,4-Tri-O-benzyl-α-L-fucopyranosyl)-(1→3)-2-acetamide-4-O-acetyl-1,5-anhydro-2,6-dideoxy-6-fluoro-D-glucitol (Hereinafter Referred to as Compound (41))

160 mg (0.212 mmol) of compound (40) was dissolved in 29 ml of n-butanol under argon atmosphere and 9 ml of ethylenediamine was added. The mixture was heated at 82° C. with stirring for 24 hours and the obtained mixture was concentrated under reduced pressure at temperatures not higher than 60° C. To the residue were added 52 ml of pyridine and then 29 ml of acetic anhydride. The reaction mixture was stirred at room temperature for 16 hours. The obtained mixture was concentrated again under reduced pressure and the residue was purified by flash chromatography (eluent; n-hexane:ethyl acetate=2:1) to give compound (41) (120 mg, 84.9%). $C_{37}H_{44}NO_9F$ (665.76)

$^{1}$H-NMR (CDCl$_3$; TMS): (7.4–7.0(m, 15H, 3Ph), 2.04(s, 3H, COCH$_3$), 1.87(s, 3H, NAc), 1.03(d, $J_{5,6}$=6.4 Hz, H-6, fucose portion).

$^{19}$F-NMR (CDCl$_3$; CFCl$_3$): δ −230(dt, JF,6H=48 Hz, JF,5H=19 Hz, 6-F, glucitol portion).

Mass spectrometry: m/z for $C_{37}H_{45}NO_9F$ Calculated: 666.3078 (M+H); Found: 666.3050

EXAMPLE 35

Synthesis of O-(2,3,4-Tri-O-benzyl-α-L-fucopyranosyl)-(1→3)-2-acetamide-1,5-anhydro-2,6-dideoxy-6-fluoro-D-glucitol (Hereinafter Referred to as Compound (42))

110 mg (0.165 mmol) of compound (41) was dissolved in 36 ml of absolute methanol under argon atmosphere and 40 mg (0.74 mmol) of sodium methoxide was added. The reaction mixture was stirred at room temperature for 6.5 hours and neutralized with a column of Amberlite IR120B ($H^+$)(eluent: methanol). The eluate was concentrated under reduced pressure and the residue was purified by flash chromatography (eluent; n-hexane:ethyl acetate=2:1) to give compound (42) (103 mg, 99.9%). $C_{35}H_{42}NO_8F$ (623.72)

IR(KBr) νmax $cm^{-1}$: 3700–3200(OH, NH), 1660, 1500 (amide), 1070(ether), 740, 700(Ph).

$^1$H-NMR ($CDCl_3$; TMS): δ 7.5–7.0(m, 15H, 3Ph), 1.85(s, 3H, NAc), 1.14(d, $J_{5,6}$=6.0 Hz, H-6, fucose portion).

$^{19}$F-NMR ($CDCl_3$; $CFCl_3$): δ −235(dt, JF,6H=47 Hz, JF,5H=23 Hz, 6-F, glucitol portion).

Mass spectrometry: m/z for $C_{35}H_{42}NO_8FNa$ Calculated: 646.2793 (M+Na); Found: 646.2799

EXAMPLE 36

Synthesis of O-(Methyl 5-acetamide-4,7,8,9-tetra-O-acetyl-3,5-dideoxy-D-glycero-α-D-galacto-2-nonulopyranosylonate)-(2→3)-O-(2,4,6-tri-O-benzoyl-β-D-galactopyranosyl-(1→4)-O-[(2,3,4-tri-O-benzyl-α-L-fucopyranosyl-(1→3)]-2-acetamide-1,5-anhydro-2,6-dideoxy-6-fluoro-D-glucitol)(Hereinafter Referred to as Compound (43))

36 mg (0.058 mmol) of compound (42) and 183 mg (0.184 mmol) of methyl O-(methyl 5-acetamide-4,7,8,9-tetra-O-acetyl-3,5-dideoxy-D-glycero-α-D-galacto-2-nonulopyranosylonate)-(2→3)-2,4,6-tri-O-benzoyl-1-thio-β-D-galactopyranoside (compound (16)) were dissolved in 2 ml of anhydrous dichloromethane under argon atmosphere. To the solution was added 140 mg of activated Molecular Sieve (4 Å). The reaction mixture was stirred at room temperature for 3.5 hours and then a mixture of 70 mg (0.27 mmol) of dimethyl(methylthio)sulfonium triflate (DMTST) and 70 mg of activated Molecular Sieve (4 Å) was added at room temperature. The obtained mixture was stirred at room temperature under argon atmosphere for 22 hours. The reaction mixture was cooled with ice and 0.36 ml of methanol and 0.18 ml of triethylamine were added, followed by stirring at room temperature for 30 minutes. The mixture was diluted with dichloromethane and then filtered and washed. A mixture of the filtrate and washing liquids was washed with water, dried over sodium sulfate and concentrated under reduced pressure. The residue was purified by silica gel column chromatography (eluent: dichloromethane→dichloromethane-methanol→100:1→50:1→30:1 (concentration gradient)) to give compound (43) (30 mg, 33.1%). $C_{82}H_{91}N_2O_{28}F$ (1571.62) $[α]_D^{24}$=−19.8° (c=1.00, chloroform)

IR(KBr) νmax $cm^{-1}$: 3400(NH), 1740, 1270(ester), 1690, 1500(amide),1070(ether), 740, 710(Ph).

$^1$NMR ($CDCl_3$; TMS): δ 8.3–7.0(m, 30H, 6Ph), 5.67(m, 1H, H-8, sialic acid portion), 5.43(dd, 1H, $J_{1,2}$=8.2 Hz, $J_{2,3}$=9.9 Hz, H-2, galactose portion), 5.23(dd, 1H, $J_{7,8}$=12.4 Hz, $J_{6,7}$=2.6 Hz, H-7, sialic acid portion), 5.13(d, 1H, $J_{1,2}$=3.7 Hz, H-1, fucose portion), 3.78(s, 3H, $OCH_3$), 2.43 (dd, 1H, $J_{3e,3a}$=12.7 Hz, $J_{3e,4}$=4.5 Hz, H-3e, sialic acid portion), 2.14–1.53(6s, 18H, 4AcO, 2AcN), 1.09(d, 3H, $J_{5,6}$=6.4 Hz, H-6, fucose portion).

$^{19}$F-NMR ($CDCl_3$; $CFCl_3$): δ −231(dt, JF,6H=46 Hz, JF,5H=21 Hz, 6-F, glucitol portion).

Mass spectrometry: m/z for $C_{82}H_{92}N_2O_{28}F$ Calculated: 1571.5821 (M+H); Found: 1571.5810

EXAMPLE 37

Synthesis of O-(Methyl 5-acetamide-4,7,8,9-tetra-O-acetyl-3,5-dideoxy-D-glycero-α-D-galacto-2-nonulopyranosylonate)-(2→3)-O-(2,4,6-tri-O-benzoyl-β-D-galactopyranosyl-(1→4)-O-[(2,3,4-tri-O-acetyl-α-L-fucopyranosyl-(1→3)]-2-acetamide-1,5-anhydro-2,6-dideoxy-6-fluoro-D-glucitol)(Hereinafter Referred to as Compound (44))

30 mg (0.019 mmol) of compound (43) was dissolved in 8 ml of ethanol and 2 ml of acetic acid and subjected to catalytic reduction in the presence of 40 mg of 10% palladium-carbon under normal hydrogen pressure at 40° C. for 16 hours. The reaction mixture was filtered and the filtrate was concentrated under reduced pressure. To the reside were added 5 ml of pyridine and 3 ml of acetic anhydride. The mixture was stirred at room temperature for 20 hours and then concentrated under reduced pressure. The residue was purified by silica gel column chromatography (eluent: chloroform→1% methanol-chloroform→2% methanol-chloroform→4% methanol-chloroform (concentration gradient)) to give compound (44) (22 mg, 80.7%). $C_{67}H_{79}N_2O_{31}F$ (1427.36) $[α]_D^{23}$=+0.8° (c=1.50, chloroform)

IR(KBr) νmax $cm^{-1}$: 3400(NH), 1740, 1230(ester), 1700, 1530(amide), 1070(ether), 720(Ph).

$^1$H-NMR ($CDCl_3$; TMS): δ 8.3–7.2(m, 15H, 3Ph), 5.75 (m, 1H, H-8, sialic acid portion), 5.48(dd, 1H, $J_{1,2}$=8.1 Hz, $J_{2,3}$=10.0 Hz, H-2, galactose portion), 5.35(d, 1H, $J_{1,2}$=3.8 Hz, H-1, fucose portion), 5.27(dd, 1H, $J_{6,7}$=2.9 Hz, $J_{7,8}$=9.9 Hz, H-7, sialic acid portion), 3.83(s, 3H, $OCH_3$), 2.41(dd, 1H, $J_{3a,3e}$=12.7 Hz, $J_{3e,4}$=4.7 Hz, H-3e, sialic acid portion), 2.17–1.56(9s, 27H, 7AcO, 2AcN), 1.11(d, 3H, $J_{5,6}$=6.5 Hz, H-6, fucose portion).

$^{19}$F-NMR ($CDCl_3$; $CFCl_3$): δ −231(dt, JF,6H=47 Hz, JF,5H=20 Hz, 6-F, glucitol portion).

Mass spectrometry: m/z for $C_{67}H_{80}N_2O_{31}F$ Calculated: 1427.4729 (M+H); Found: 1427.4705

EXAMPLE 38

Synthesis of o-(5-Acetamide-3,5-dideoxy-D-glycero-α-D-galacto-2-nonulopyranosylonic acid)-(2→3)-O-β-D-galactopyranosyl-(1→4)-O-[α-L-fucopyranosyl-(1→3)]-2-acetamide-1,5-anhydro-2,6-dideoxy-6-fluoro-D-glucitol) (Hereinafter Referred to as Compound (45))

19 mg (0.013 mmol) of compound (44) was dissolved in 1.5 ml of methanol anhydride under argon atmosphere and 3 mg (0.06 mmol) of sodium methoxide was added. The mixture was stirred at room temperature for 24 hours and then 0.9 ml of water was added, followed by further stirring for 7.5 hours. The mixture was neutralized with a column of Amberlite IR120B($H^+$)(eluent: methanol) and concentrated under reduced pressure. The residue was purified by gel filtration column chromatography on Sephadex LH20 (10 g) to give compound (45) (6.0 mg, 55.9%). $C_{31}H_{51}N_2O_{21}F$ (806.74) $[α]_D^{23}$=−30.5° (c=0.22, methanol)

IR(KBr) νmax $cm^{-1}$: 3700–3200(OH, NH), 1730 (carboxylic acid), 1630, 1560(amide), 1070(ether).

$^1$H-NMR ($CDCl_3$; TMS): δ 5.10(d, 1H, $J_{1,2}$=3.5 Hz, H-1, fucose portion) 4.27(d, 1H, $J_{1,2}$=7.8 Hz, galactose portion), 2.80(dd, 1H, $J_{3a,3e}$=12.2 Hz, $J_{3e,4}$=4.8 Hz, H-3e, sialic acid portion), 1.97, 1.95(2s, 6H, 2AcN), 1.12(d, 3H, $J_{5,6}$=6.7 Hz, H-6, fucose portion).

$^{19}$F-NMR ($CDCl_3$; $CFCl_3$): δ −230(dt, JF,6H=48 Hz, JF,5H=29 Hz, 6-F, glucositol portion).

Mass spectrometry: m/z for $C_{31}H_{51}N_2O_{21}FNa$ Calculated: 806.2866 (M+Na); Found: 806.2854 Elemental analysis: $C_{31}H_{51}N_2O_{21}FNa$ Calculated: C; 46.15, H; 6.37, N; 3.47; Found: C; 46.00, H; 6.66, N; 3.33.

Pharmacological Test Example 1: Metabolic Stability Test

Used as substrates were natural sialyl Lewis X Ganglioside (SLeX Ganglioside) and compound 24 of the invention obtained in Example 19.

The structures of compound 24 and SLeX Ganglioside are shown below.

Compound 24

SLeX Ganglioside

Compound 24 and SLeX Ganglioside (30 mmol each) were separately dissolved in 0.1 ml of distilled water, followed by addition of 0.02 ml of α-fucosidase ammonium sulfate suspension (product of Wako Pure Chemical Industries, Ltd.; at least 2 units/mg protein). Then 0.5, 1.0, 2.0 and 3.0 min. later, each reaction aqueous solution was spotted on a silica gel TLC plate (5715, product of Merk Co.). The TLC plate was developed until the reaction solution front moved 2 cm (developing solvent; n-butanol:acetic acid:water=8:5:4). After immersion in phosphomolybdic acid.phosphoric acid.sulfonic acid mixed aqueous solution, the plate was heated to develop colors and the amount of the remaining substrate was measured.

Shown below are rates of flow (Rf) on the TLC plate, of compound 24, SLeX Ganglioside (substrates) and those decomposed by α-fucosidase.

| Compound | Rf |
|---|---|
| SLeX Ganglioside | 0.75 |
| Decomposed SLeX Ganglioside | 0.20 |
| Compound 24 | 0.75 |
| Decomposed Compound 24 | 0.25 |

With a mass spectrometer, it was confirmed that α-fucosidase decomposed compound 24 and SLeX Ganglioside into the corresponding fucose-cleaved derivatives.

The results are shown in Table 1 and FIG. 1.

TABLE 1

Substrate decomposition reaction by α-fucosidase
Remaining Syalyl Lewis X (%)

| Time (min.) | SLeX Ganglioside | Compound 24 |
|---|---|---|
| 0 | 1.0 | 1.0 |
| 0.5 | 0.2 | 0.5 |
| 1.0 | 0.0* | 0.2 |
| 2.0 | — | 0.05 |
| 3.0 | — | 0.0* |

*With the TLC color development, complete vanishment of the spot of the substrate was confirmed.

The results of Table 1 prove improved stability of the compound of the invention against α-fucosidase.

That is, a natural sialyl Lewis X Ganglioside (SLeX Ganglioside) quickly decomposes in the presence of α-fucosidase, whereas compound 24 having fluorine in place of hydroxyl at 6-position of N-acetylglucosamine more strongly resists the decomposition by α-fucosidase than a natural Ganglioside.

What is claimed is:

1. A Lewis X derivative represented by the following formula (I):

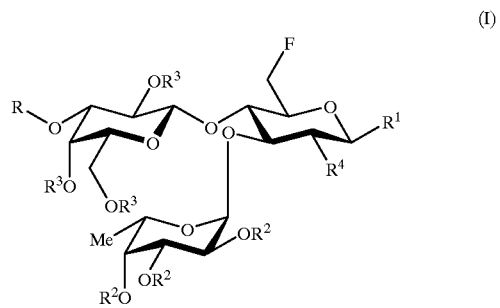

(I)

wherein R represents $-PO(OH)_2$, $-SO_3H$ or sialylate represented by formula (III)

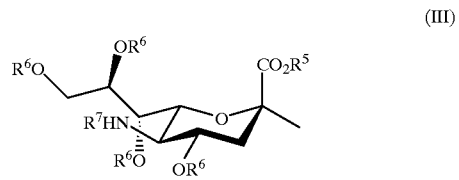

(III)

wherein $R^5$ represents hydrogen, lower alkyl, sodium, potassium or quaternary ammonium, $R^6$ represents hydrogen, aliphatic acyl or aromatic acyl and $R^7$ represents aliphatic acyl;

$R^1$ represents aliphatic acyloxy, aromatic acyloxy, lower alkylthio, optionally substituted phenylthio, branched long chain alkoxy, optionally substituted phenylmethoxy or formula (IV)

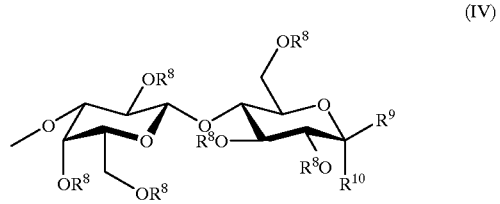

(IV)

wherein $R^8$ represents hydrogen, aliphatic acyl, aromatic acyl or optionally substituted phenylmethyl, $R^9$ represents hydrogen, hydroxyl, trialkylsilylethoxy or sphingosinyl represented by formula (V)

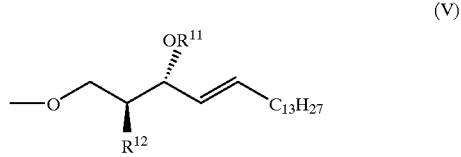

(V)

wherein $R^{11}$ represents hydrogen or benzoyl, $R^{12}$ represents azide, amine or $-NHCOR^{13}$ and $R^{13}$ represents $C_{15\text{-}25}$ aliphatic alkyl, and $R^{10}$ represents hydrogen or —O—C(=NH)CCl$_3$, provided that when $R^{10}$ is —O—C(=NH)CCl$_3$, $R^9$ is hydrogen;

$R^2$ and $R^3$ may be the same or different and independently represent hydrogen, aliphatic acyl, aromatic acyl or optionally substituted phenylmethyl; and $R^4$ represents aliphatic acylamino or aromatic acylamino.

2. The sialyl Lewis X derivative according to claim 1 which is represented by the following formula (VI):

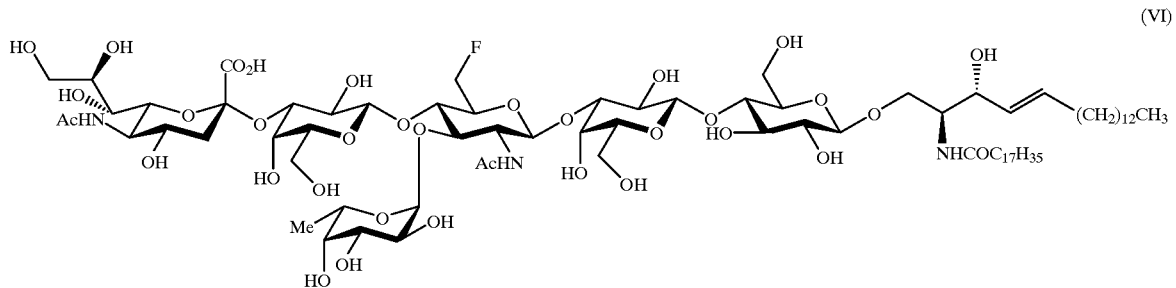
(VI)

wherein Ac represents acetyl and Me represents methyl.

3. The sialyl Lewis X derivative according to claim 1 which is represented by the following formula (VII):

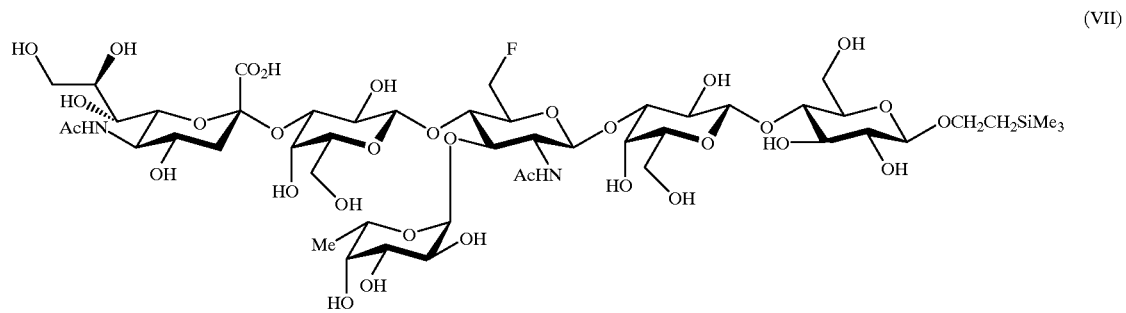
(VII)

wherein Ac represents acetyl and Me represents methyl.

4. The sialyl Lewis X derivative according to claim 1 which is represented by the following formula (VIII):

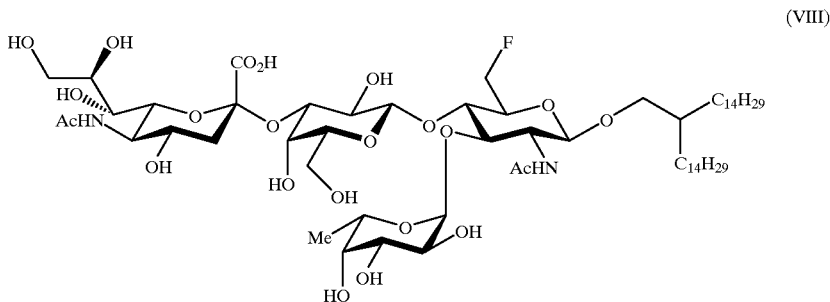
(VIII)

wherein Ac represents acetyl and Me represents methyl.

5. The sialyl Lewis X derivative according to claim 1 which is represented by the following formula (X):

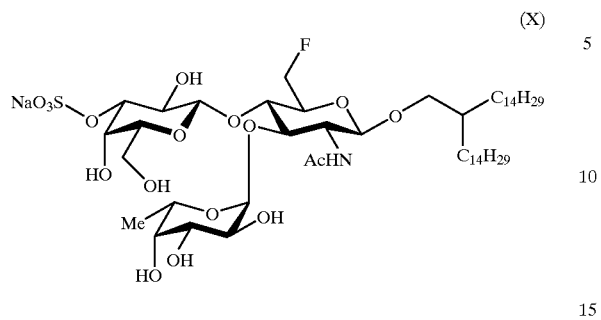
(X)

wherein Ac represents acetyl and Me represents methyl.

6. An intermediate for synthesis of a sialyl Lewis X derivative or a Lewis X derivative, which is represented by the following formula (II):

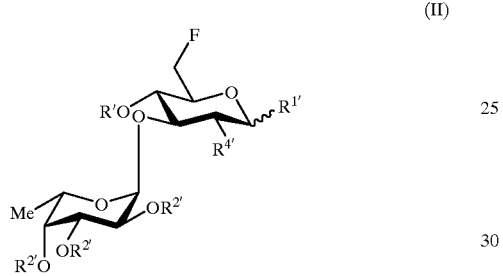
(II)

wherein R' represents hydrogen, aliphatic acyl or aromatic acyl; $R^{1'}$ represents optionally substituted phenylmethoxy, aliphatic acyloxy, aromatic acyloxy, lower alkylthio, optionally substituted phenylthio, or branched long chain alkoxy;

$R^{2'}$ represents hydrogen, optionally substituted phenylmethyl, aliphatic acyl or aromatic acyl; and $R^{4'}$ represents optionally substituted phthalimide, aliphatic acyloxy, aromatic acyloxy, aliphatic acylamino or aromatic acylamino.

7. The synthetic intermediate according to claim 6 which is represented by any one of the following formulae (XI), (XII) and (XIII):

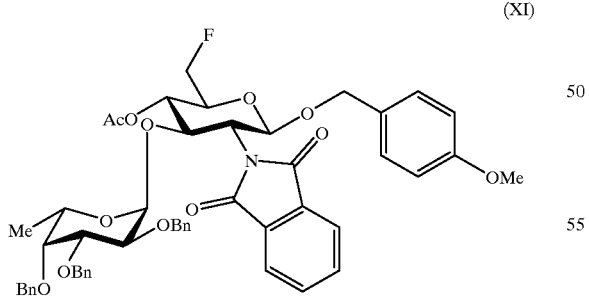
(XI)

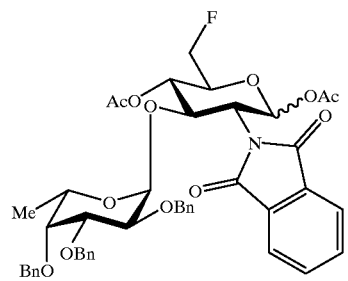
(XII)

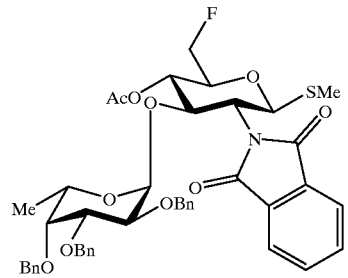
(XIII)

wherein Ac represents acetyl, Me represents methyl and Bn represents benzyl.

8. The synthetic intermediate according to claim 6 which is represented by the following formula (XVI):

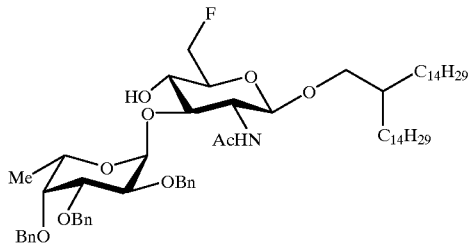
(XVI)

wherein Ac represents acetyl, Me represents methyl and Bn represents benzyl.

* * * * *

UNITED STATES PATENT AND TRADEMARK OFFICE
CERTIFICATE OF CORRECTION

PATENT NO. : 6,084,081
DATED : July 4, 2000
INVENTOR(S) : Ohira et al.

Page 1 of 1

It is certified that error appears in the above-identified patent and that said Letters Patent is hereby corrected as shown below:

Column 59,
Lines 39-40, "aliphatic acyloxy, aromatic acyloxy" should be deleted

Signed and Sealed this

Thirteenth Day of November, 2001

Attest:

NICHOLAS P. GODICI
Attesting Officer        Acting Director of the United States Patent and Trademark Office